US012330154B2

United States Patent
Blainey et al.

(10) Patent No.: US 12,330,154 B2
(45) Date of Patent: Jun. 17, 2025

(54) REACTION CIRCUIT DESIGN IN MICROFLUIDIC CIRCUITS

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); Son Hoang, Cambridge, MA (US); Huaibin (Eli) Zhang, Cambridge, MA (US); Jillian Nolan, Cambridge, MA (US); Soohong Kim, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 21 days.

(21) Appl. No.: 17/871,135

(22) Filed: Jul. 22, 2022

(65) Prior Publication Data

US 2022/0362770 A1 Nov. 17, 2022

Related U.S. Application Data

(62) Division of application No. 15/553,961, filed as application No. PCT/US2016/019606 on Feb. 25, 2016, now Pat. No. 11,406,980.

(Continued)

(51) Int. Cl.
*B01L 3/00* (2006.01)
*C12N 15/10* (2006.01)
(Continued)

(52) U.S. Cl.
CPC ....... *B01L 3/502738* (2013.01); *B01L 3/5025* (2013.01); *B01L 3/502715* (2013.01);
(Continued)

(58) Field of Classification Search
CPC ............. B01L 3/502738; B01L 3/5025; B01L 3/502715; B01L 3/502723; B01L 3/50273;
(Continued)

(56) References Cited

U.S. PATENT DOCUMENTS

2003/0206806 A1 11/2003 Paul et al.
2006/0006065 A1 1/2006 Pinkas et al.
(Continued)

FOREIGN PATENT DOCUMENTS

WO 2015050998 A2 4/2015

OTHER PUBLICATIONS

Invitation to Pay Additional Fees for PCT Application No. PCT/US2016/019606, mailed May 9, 2016, 2 pages.
(Continued)

*Primary Examiner* — Rebecca M Fritchman
(74) *Attorney, Agent, or Firm* — Day Pitney LLP; Richard B. Emmons; Christopher R. Cowles

(57) ABSTRACT

The microfluidic devices and systems disclosed herein reduce sample loss and help decrease sample processing bottlenecks for applications such as next generation sequencing (NGS). The microfluidic devices include a plurality of reaction modules. Each reaction module may comprise one or more reaction circuits. Each reaction circuit may comprise a single reaction flow channel with each reaction circuit connected by a bridge flow channel. Alternatively, each reaction circuit may comprise two or more reaction flow channels connected by two or more bridge flow channels. The combination of any two bridge flow channels and (Continued)

a portion of the two or more reaction flow channels between the any two bridge flow channels defining may define the reaction circuit. The reaction module may be arranged as nodes connected by bridge flow channels or each reaction module may be arranged in a parallel fashion on the microfluidic device.

19 Claims, 15 Drawing Sheets

Related U.S. Application Data

(60) Provisional application No. 62/120,738, filed on Feb. 25, 2015.

(51) Int. Cl.
  *C12Q 1/6837* (2018.01)
  *F04B 19/00* (2006.01)
  *F16K 99/00* (2006.01)

(52) U.S. Cl.
  CPC ..... *B01L 3/502723* (2013.01); *B01L 3/50273* (2013.01); *C12N 15/1065* (2013.01); *C12Q 1/6837* (2013.01); *F04B 19/006* (2013.01); *F16K 99/0015* (2013.01); *F16K 99/0057* (2013.01); *F16K 99/0059* (2013.01); *B01J 2219/00398* (2013.01); *B01J 2219/00495* (2013.01); *B01J 2219/00585* (2013.01); *B01J 2219/0059* (2013.01); *B01J 2219/00689* (2013.01); *B01J 2219/00722* (2013.01); *B01L 2200/10* (2013.01); *B01L 2200/143* (2013.01); *B01L 2200/16* (2013.01); *B01L 2300/027* (2013.01); *B01L 2300/0681* (2013.01); *B01L 2300/0861* (2013.01); *B01L 2300/0864* (2013.01); *B01L 2300/0867* (2013.01); *B01L 2300/087* (2013.01); *B01L 2300/123* (2013.01); *B01L 2400/0481* (2013.01); *B01L 2400/0655* (2013.01); *F16K 2099/0084* (2013.01); *F16K 2099/0086* (2013.01)

(58) Field of Classification Search
  CPC .......... B01L 2200/10; B01L 2200/143; B01L 2200/16; B01L 2300/027; B01L 2300/0681; B01L 2300/0861; B01L 2300/0864; B01L 2300/0867; B01L 2300/087; B01L 2300/123; B01L 2400/0481; B01L 2400/0655; C12N 15/1065; C12Q 1/6837; F04B 19/006; F16K 99/0015; F16K 99/0057; F16K 99/0059; F16K 2099/0084; F16K 2099/0086; B01J 2219/00398; B01J 2219/00495; B01J 2219/00585; B01J 2219/0059; B01J 2219/00689; B01J 2219/00722
  See application file for complete search history.

(56) References Cited

U.S. PATENT DOCUMENTS

| | | | |
|---|---|---|---|
| 2008/0053543 A1* | 3/2008 | Baier | G01N 30/20 137/625.25 |
| 2008/0277494 A1 | 11/2008 | Davies et al. | |
| 2008/0281090 A1* | 11/2008 | Lee | B01J 19/0093 422/600 |
| 2014/0065653 A1* | 3/2014 | Maerkl | B81C 1/00119 137/561 A |
| 2014/0287966 A1* | 9/2014 | Gray | G01N 21/01 506/39 |
| 2015/0352544 A1 | 12/2015 | Buermann et al. | |
| 2016/0114322 A1 | 4/2016 | Ismagilov et al. | |

OTHER PUBLICATIONS

International Search Report and Written Opinion for PCT Application No. PCT/US2016/019606, mailed Jul. 26, 2016, 21 pages.

* cited by examiner

240

(top)
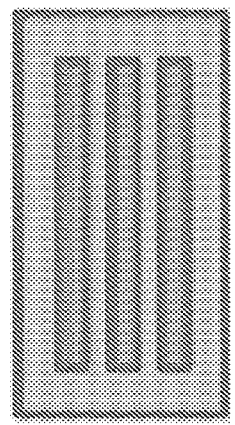
(side)
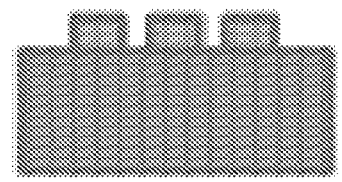
FIG. 6

REACTION CIRCUIT DESIGN IN MICROFLUIDIC CIRCUITS

CROSS-REFERENCE TO RELATED APPLICATIONS

This application is a divisional of application Ser. No. 15/553,961 filed Aug. 25, 2017, which is a U.S. National Stage application of International Patent Application No. PCT/US2016/019606 filed Feb. 25, 2016, which claims the benefit of U.S. Provisional Application No. 62/120,738 filed Feb. 25, 2015. The entire contents of the above-identified applications are hereby fully incorporated herein by reference.

TECHNICAL FIELD

The subject matter disclosed herein is generally related to microfluidic devices, control systems for microfluidic devices, and methods of using the same. Specifically, the microfluidic devices and systems disclosed herein reduce sample loss and help decrease sample processing bottlenecks for applications such as next generation sequencing (NGS).

BACKGROUND

There is a tremendous need to conduct research studies and clinical sequencing with larger numbers of samples and increasingly complex sample preparation. Genome-wide association studies for complex genetic disease require extremely large cohorts. At the same time, sequence-based clinical diagnostics are applicable to millions of patients in the US (e.g. non-invasive prenatal) and there is an emerging trend in clinical genomics to obtain larger numbers of samples from each subject, either as a function of space or of time (e.g. for ongoing observation of a patient). Finally, the rise of single-cell analysis in mainstream research represents the ultimate in sample count increase and sample preparation complexity, as single-cell techniques transform an individual conventional sample into a much larger number of individual sub-samples (the single cells).

The intense focus on development of ever-higher-throughput sequence readout methods over the last decade has been wildly successful. Even so, many investigators are prioritizing high sample throughput over sequencing depth to drive statistical power in studies and control cost per sample. Alarmingly, further improvements in sequence readout technology will show diminishing returns in enabling high sample throughput human genomics unless looming upstream bottlenecks are addressed.

Sequence readout cost and total project cost are decoupling because the cost of sample preparation remains several hundred dollars per sample even as the cost of sequence readout has dropped below $1000 per sample for many applications. Despite the emergence of sample preparation as a relevant NGS cost driver, technology development for sample preparation has not been pursued with the same vigor as technology development for sequence readout.

Exome sequencing and ChIP-Seq require lower quantities of sequence data and relatively more complex sample preparation protocols. These applications are already 'sample-preparation-limited' on the HiSeq2500 platform with library construction (LC) alone constituting more than 50% of total assay cost. Even human WGS sequencing is significantly affected now, with 30% of 15×WGS costs attributable to library construction on HiSeqX. Anticipating further improvements in sequence readout technology, all sequencing applications will soon become sample-prep-limited if robust new technologies for sample preparation are not developed and deployed. Miniaturization, process integration/automation, and control of capital and consumables costs are required to achieve significant sample preparation cost reduction.

SUMMARY

In one aspect, the embodiments described herein are directed to microfluidic devices comprising a plurality of reaction modules. Each reaction module may comprise one or more reaction circuits. Each reaction circuit may comprise a single reaction flow channel with each reaction circuit connected by a bridge flow channel. Alternatively, each reaction circuit may comprise two or more reaction flow channels connected by two or more bridge flow channels. The combination of any two bridge flow channels and a portion of the two or more reaction flow channels between the any two bridge flow channels may define a reaction circuit. The reaction module may be arranged as nodes connected by bridge flow channels or each reaction module may be arranged in a parallel fashion on the microfluidic device.

The reaction flow channels and the bridge flow channels may comprise one or more valves and one or more filters. The valves may be formed of an elastomeric material that can be deflected into the reaction flow channel by the application of pressure. Filters may be designed to filter based on size and may function similarly to valves except that the filters only partially block a reaction or bridge flow channel when pressure is applied.

In another aspect, embodiments disclosed herein are directed to microfluidic controller systems for controlling operation of the microfluidic devices. The system may comprise one or more microfluidic devices and a controller. The controller comprises at least one set of programmable valves. In certain example embodiments, each set of programmable valves is under the control of a separate control board. In one example embodiment, the second set of programmable valves is connected to a programmable regulator, which allows for pressure adjustments to be made to the microfluidic device while the device is in use. The controller system also includes a graphical user interface (GUI) that can generate a virtual microfluidic device architecture showing the positioning of microfluidic device component parts, such as valves and filters. The component parts can be selected and operation values such as pressure modified on the GUI.

In another aspect, embodiments disclosed herein are directed to methods of closed-loop tuning of microfluidic devices. A device comprising one or more elements that are pressure sensitive can be attached to the controller systems described herein. Machine vision imaging and/or flow sensor with controlled feedback can be used to monitor the elements on the microfluidic device surface. The controller system can then expose the one or more elements element to a series of differing pressures. The machine vision imaging or flow sensor with controlled feedback may then be used to confirm the optimal pressure at which the element functions properly.

In another aspect, embodiments disclosed herein are directed to the processing of samples, in particular biological samples. For example, the methods disclosed herein can be used to prepare small sample volumes with minimal sample loss for downstream analysis, such as sample preparation for nucleic acid sequencing using next generation sequencing technologies.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 6 is a diagram depicting and example filter design, in accordance with certain example embodiments.

DETAILED DESCRIPTION OF THE EXAMPLE EMBODIMENTS

Overview

Figure 1:
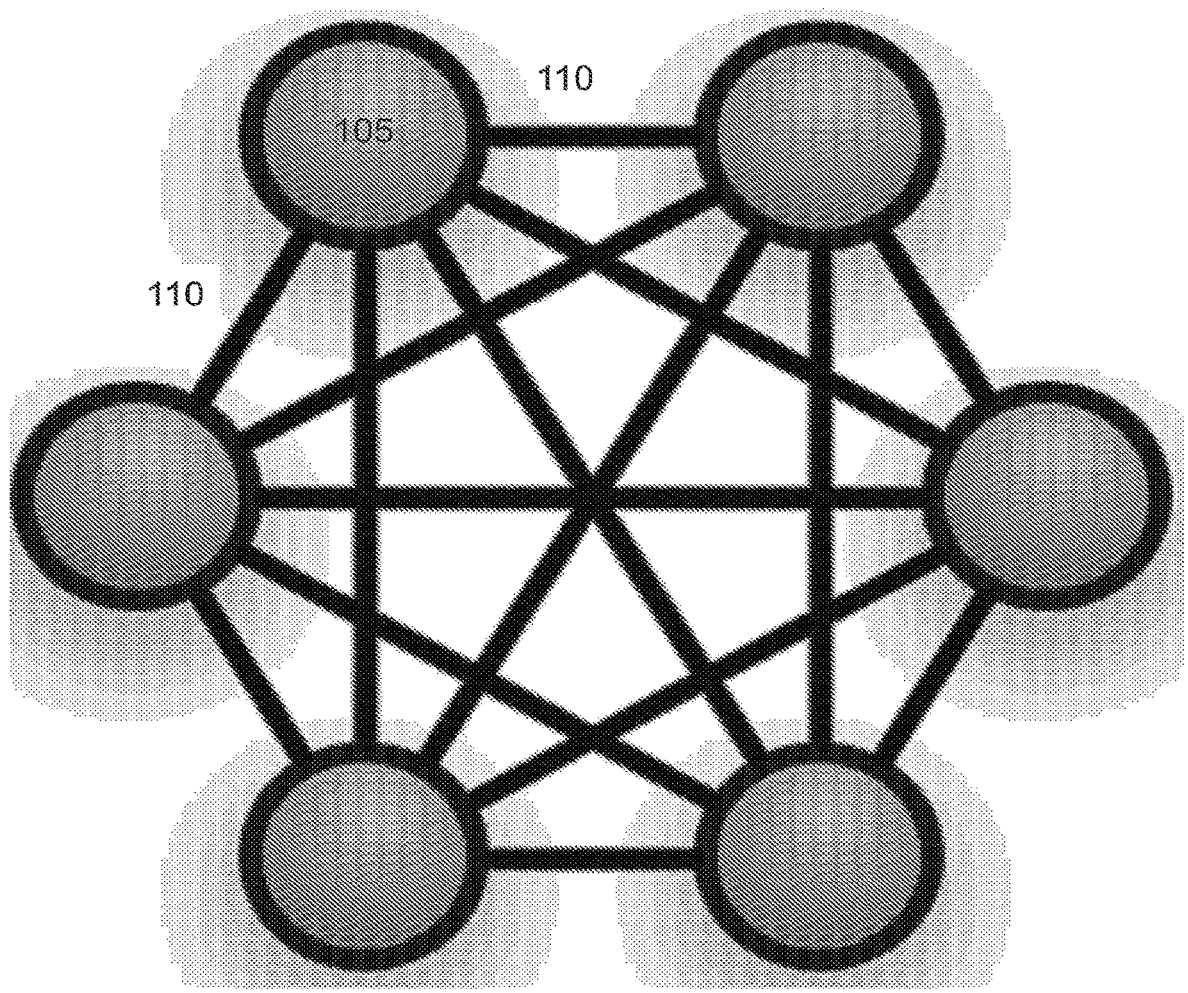
FIG. 1 is a diagram depicting an example node-based topology of reaction modules, in accordance with certain example embodiments.

Sequencing applications demand ever-increasing data quantity and quality from limited input material. Read-out by next-generation sequencing (NGS) no longer limits throughput for many project types. Three trends point to sample preparation as an increasingly restrictive bottleneck in future NGS workflows; continuing reduction in readout cost, increasingly complex sample preparation for more advanced assays, such as single-cell assays, and demand for higher sample throughput in research and clinical applications. Embodiments herein provide microfluidic devices and controller systems that enable low-cost genomic, epigenetic, functional genomic, and multi-omic sample preparation.

Embodiments herein provide microfluidic devices comprising one or more reaction modules, with each module comprising one or more reaction circuits. The microfluidic devices disclosed herein allow multiple reagents to be loaded and mixed without requiring removal of sample. Sample loss is avoided, for example, by redirecting the sample into another reaction circuit when new reagents are loaded on the microfluidic device. In addition, the reaction circuits disclosed herein allow for new device capabilities such as multi-tier mixing and filtering. The new designs allow capture substrates to be re-suspended in solution and filtered again. The ability to repeat washes on the fly dramatically improves capture substrate washing efficiency and uniformity. In addition, the reaction modules described herein allow for more flexible fluid pathways and better utilization of microfluidic device architecture and components.

Embodiments herein further provide controller systems for microfluidic devices that provide a portable system with at least two sets of programmable valves that can be used to provide a series of different pressure inputs to a microfluidic device or set of microfluidic devices run in parallel. The controller also provides the ability for on the fly modifications to operating pressures on the chip. For example, most microfluidic devices have a standard operating pressure, however that pressure can change during operation of the microfluidic device. The microfluidic device controller systems disclosed herein enable the ability to do on the fly pressure regulation to account for these fluctuations. In addition to on the fly pressure regulation, the controller systems also enable closed-loop tuning of microfluidic devices. For example, certain component parts of microfluidic devices, such as valves and filters, have a manufacturing tolerance for certain pressures at which they will function properly. However, those tolerances may not be readily known. For example, sensors and other monitoring devices, such as pressure sensors, heat sensors or any other device to measure a control parameter may provide readings to the controller, which in turn may automatically adjust the conditions of the system, such as pressure, temperature or the like to be within specific ranges. As such, an automatic feedback control may be established. Additionally, the controller system may offer "manual" (non-automatic) control of the parameters so that such adjustments may be made by an operator via an appropriate interface with the controller, such as a graphical user interface (GUI) or other known adjustment mechanism. For example, adjustment to the pressure regulator by direct interface with the pressure regulator control (e.g., a knob or digital meter). The controller system can run software protocols that monitor a microfluidic device connected to the system and expose individual components to differing pressures to determine the optimal operating pressure for each component. The controller systems also include a graphical user interface (GUI) which provides a virtual representation of the microfluidic device architecture, allowing for adjustments to certain components of the microfluidic device by selection of the corresponding component part on the GUI.

Microfluidic Devices

In one aspect, the embodiments herein are directed to microfluidic devices with a plurality of reaction modules, which may be connected via a plurality of bridges and/or valves. Each reaction module may comprise one or more reaction circuits. A reaction circuit may be defined by a single reaction flow channel with one or more valves that allow flow of a fluid in a defined pattern in the reaction circuit. Alternatively, the reaction circuit may be formed from two or more reaction flow channels connected together at two or more points. In certain example embodiments, two or more reaction flow channels may be connected by bridge flow channels. In certain example embodiments, the plurality of reaction circuits employ a "ladder" design or stack of connected reaction circuits that resemble the shape of a ladder. In this metaphor, the rails of the ladder are the reaction flow channels, and the rungs of the ladder are the bridge flow channels. Each reaction circuit may further comprise one or more filters. Each reaction module thus may include one or more possible flow paths that may form a reaction circuit as defined by the operation of selected combinations of valves and/or filters. Such reaction circuits may be changed dynamically during operation to allow samples to flow into circuits of different volumes during the course of the same assay process.

Figure 3:
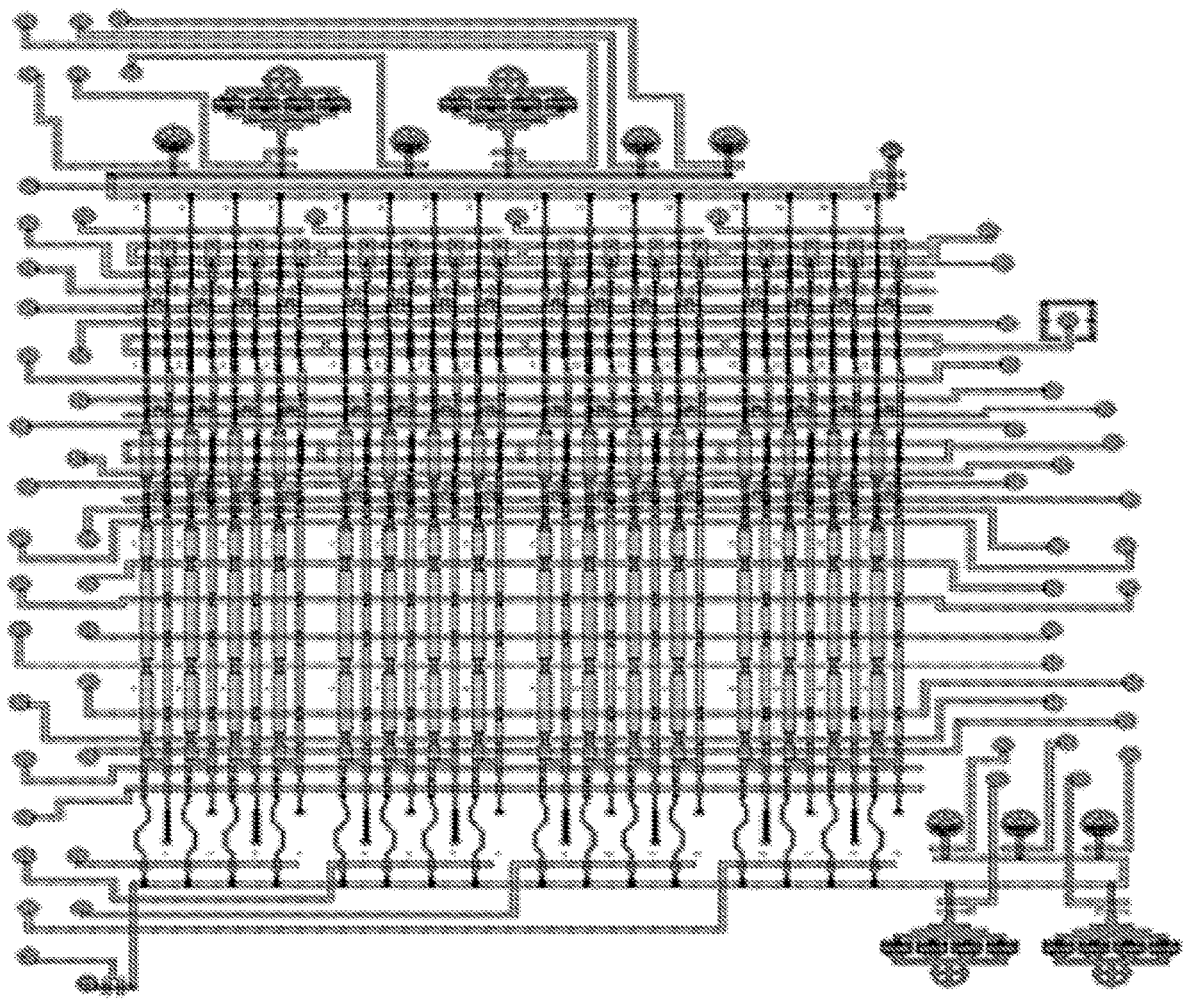
FIG. 3 is a diagram depicting an example microfluidic device topology comprising multiple reaction modules arranged in a parallel fashion, in accordance with certain example embodiments.

The reaction modules comprising one or more reaction circuits may be formed in a networked fashion on the microfluidic device with each node in the network representing a reaction module with one or more reaction circuits. An example network topology is shown in FIG. 1, however the network topology may vary. The reaction modules comprising one or more reaction circuits may also be arranged in a parallel fashion on the microfluidic device. See FIG. 3.

Figure 2:
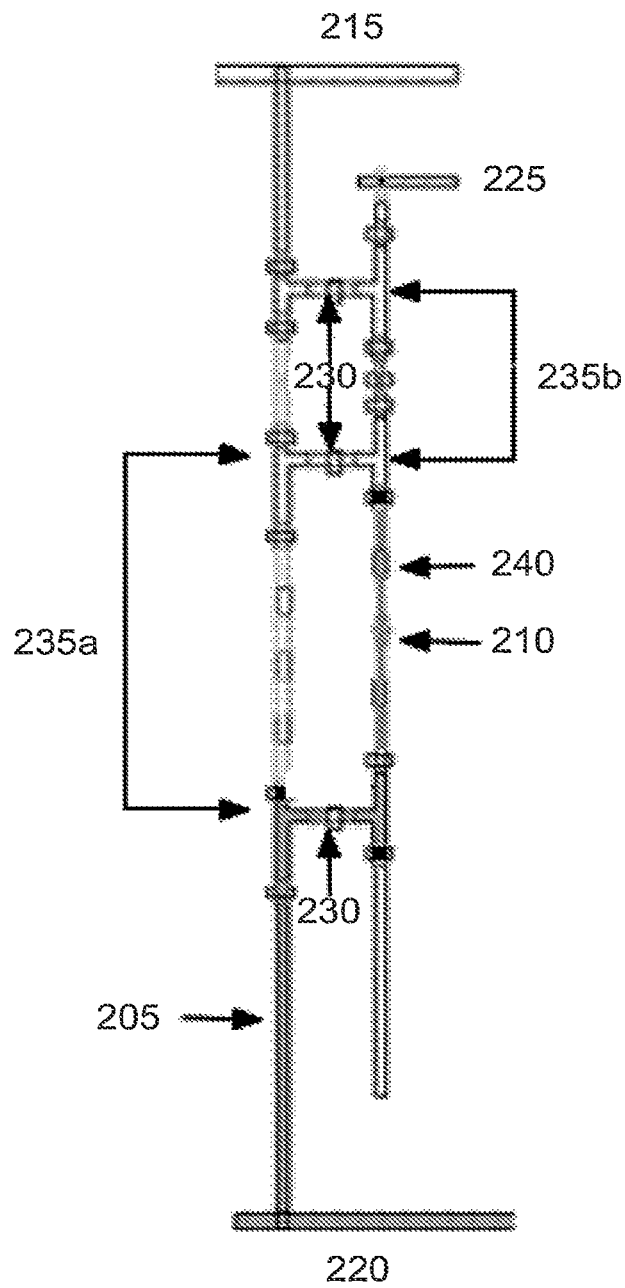
FIG. 2 is a diagram depicting an example "ladder" reaction module design comprising two reaction circuits, in accordance with certain example embodiments.

Referring now to FIG. 2, in one example embodiment, the microfluidic device comprises a first reaction flow channel 205 and a second reaction flow channel 210. The first reaction flow channel 205 may be connected at a first end to a first input 215 and connected at a second end to a second input 220. The second reaction flow 210 channel may be connected at a first end to an output 225. The configuration in FIG. 2 is an example only, and other configurations of inputs and outputs are possible. Likewise, one of ordinary skill in the art will recognize that the designation as an input and output is relative to the direction a solution is loaded onto and off a reaction module such that what may be designated an input in one protocol may function as an output in another protocol and vice versa.

The first and second reaction flow channels may be connected by three or more bridge flow channels 230. The first and second reaction flow channels 205, 210 and the bridge flow channels 230 may comprise one or more valves/filters 240. A valve may fully restrict a flow channel, whereas a filter may comprise a valve that does not fully restrict flow in a flow channel, or other appropriate structure.

Figure 12:
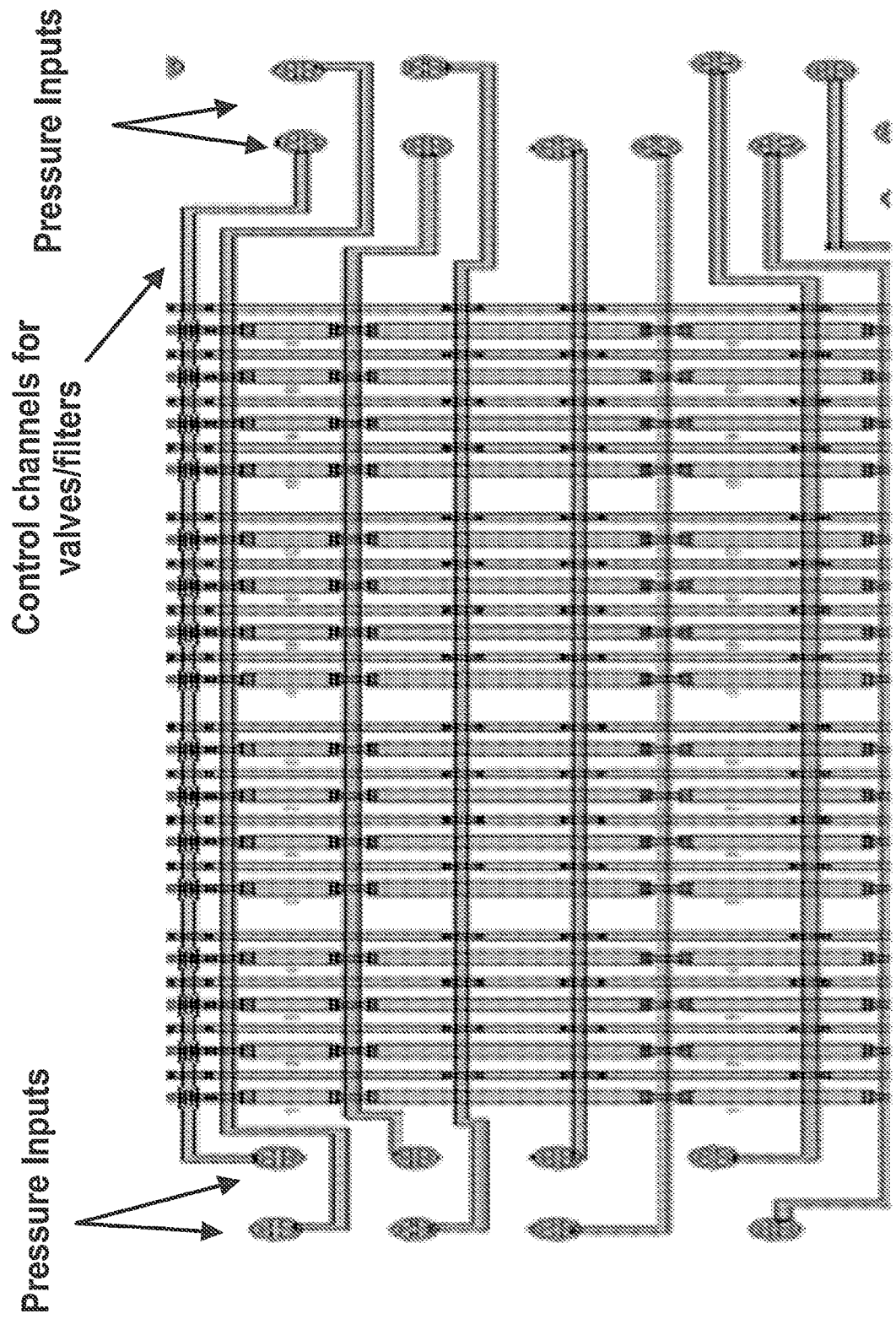
FIG. 12 is a diagram depicting a section of microfluidic device topology comprising multiple reaction modules arranged in parallel, in accordance with certain example embodiments.

A reaction circuit 235 is defined by any two bridge flow channels and the portions of the first and second reaction flow channels between the any two bridge flow channels. The valves are arranged such that access to a portion of the first or second reaction flow channels in a reaction circuit can be filled with a fluid independently of other components on the reaction module. The valves are also arranged such that fluids can be circulated within one reaction circuit independently of other reaction circuits. The reaction circuits may be the same size or vary in size. The reaction circuit 235 may also comprise one or more filters 240. In addition, the reaction circuits 235 may comprise one or more pumps. For example, peristaltic pumping can be achieved by controlling the open/close sequence of a set of valves. In certain example embodiments, the control channel for each set of valves or filters has pressure inputs on opposite ends thereof, such as on the left and right sides of the microfluidic device. The use of two pressure inputs allows for uniform mixing across the chip by increasing valve actuation time and avoiding delay from the build-up of pressure gradients between reaction circuits across the chip. See FIG. 12.

In certain example embodiments, a reaction module may comprise between 1 and 10 reaction circuits. In certain example embodiments, the microfluidic device may comprise between approximately 1 and 384, between approximately 1 and 192, between approximately 1 and 144, between 1 and approximately 96, between 1 and approximately 48, between 1 and approximately 24, between one and approximately 12 reaction modules. Within the spirit and scope of the present invention, the number of reaction modules may be scaled as necessary and chip layout adjusted accordingly for the number of reactions to be performed. In one example embodiment, the microfluidic device has 96 reaction modules. See FIG. 3 for an example arrangement of reaction modules comprising multiple reaction circuits per reaction module. The reaction modules disclosed herein may be arranged in a similar fashion. The number of reaction circuits on a microfluidic device is limited by the size considerations of the microfluidic device and the type of assay to be conducted on the device. The number of reaction circuits listed is exemplary and reflects the number of reaction modules that may be incorporated in certain designs. However, as one of ordinary skill in the art would recognize, increasing the overall size of the microfluidic device may allow for additional reaction modules to be incorporated.

Reaction flow channels may have a length of approximately 0.5 mm to approximately 30 mm and an average width of 0.05 mm to 0.5 mm. In certain example embodiments the first reaction flow channel 205 has a length of approximately 1 mm to approximately 10 mm, and the second reaction flow channel 210 has a length of approximately 1 mm to approximately 10 mm. In certain example embodiments, the reaction flow channels may have a substantially rectangular profile. The bridge flow channels may have a length of approximately 0.2 mm to approximately 1 mm and an average width of approximately 0.1 mm to approximately 0.4 mm. Reaction flow channels may maintain the same width throughout or may vary in width along the length of the reaction or bridge flow channel.

Reaction and bridge flow channels may have a width of 0.05 mm to 1 mm. In certain example embodiments, the reaction flow channels have a length of 0.05 mm to 0.9 mm, 0.05 mm to 0.8 mm, 0.05 mm to 0.7 mm, 0.05 mm to 0.6 mm, 0.05 mm to 0.5 mm, 0.05 mm to 0.4 mm, 0.05 mm to 0.3 mm, 0.05 mm to 0.2 mm, 0.05 mm to 0.1 mm, 0.05 mm to 0.09 mm, 0.05 mm to 0.08 mm, 0.05 mm to 0.07 mm, 0.05 mm to 0.06 mm, 0.1 mm to 1 mm, 0.2 mm to 1 mm, 0.3 mm to 1 mm, 0.4 mm to 1 mm, 0.5 mm to 1 mm, 0.6 mm to 1 mm, 0.7 mm to 1 mm, 0.8 mm to 1 mm, or 0.9 mm to 1 mm. In another example embodiment, the reaction and bridge flow channels may have a width selected from the group consisting of: between 1 μm and about 5 μm, between 5 μm and about 25 μm, between 25 μm and 50 μm, between 50 μm and 75 μm, between 75 μm and 100 μm, between 100 μm and 125 μm, between 125 μm and 175 μm, between 175 μm and 225 μm, between 200 μm and 225 μm and between 225 μm and 250 μm, between 250 μm and 275 μm, and between 275 μm and 300 μm.

The reaction and bridge flow channels may have a height of between 5 μm and 10 μm, between 10 μm and 15 μm, between 15 μm and 20 μm, between 20 μm and 25 μm, between 25 μm and 30 μm, between 30 μm and 35 μm, between 35 μm and 40 μm, between 40 μm and 45 μm, between 45 μm and 50 μm, between 50 μm and 55 μm, between 10 μm and 400 μm, between 20 μm and 400 μm, between 30 μm and 400 μm, between 40 μm and 400 μm, between 50 μm and 400 μm, between 60 μm and 400 μm, between 70 μm and 400 μm, between 80 μm and 400 μm, between 100 μm and 400 μm, between 125 μm and 400 μm, between 150 μm and 400 μm, between 175 μm and 400 μm, between 200 μm and 400 μm, between 225 μm and 400 μm, between 250 μm and 400 μm, between 275 μm and 400 μm, between 300 μm and 400 μm, between 325 μm and 400 μm, between 350 μm and 400 μm, and between 375 μm and 400 μm.

The reaction and bridge flow channels can have an aspect of height to width of less than about 1:2, less than about 1:5, less than about 1:10, and less than about 1:15.

A reaction circuit may have a volume of 40 nL to 5000 nL, 40 nL to 4500 nL, 40 nL to 4000 nL, 40 nL to 3500 nL, 40 nL to 3000 nL, 40 nL to 2500 nL, 40 nL to 2000 nL, 40 nL to 1500 nL, 40 nL to 1000 nL, 40 nL to 900 nL, 40 nL to 800 nL, 40 nL to 700 nL, 40 nL to 600 nL, 40 nL to 500 nL, 40 nL to 400 nL, 40 nL to 300 nL, 40 nL to 200 nL, 40 nL to 100 nL, 40 nL to 90 nL, 40 nL to 80 nL, 40 nL to 70 nL, 40 nL to 60 nL, 40 nL to 50 nL, 50 nL to 60 nL, 50 nL to 70 nL, 50 nL to 80 nL, 50 nL to 90 nL, 50 nL to 100 nL, 50 nL to 200 nL, 50 nL to 300 nL, 50 nL to 400 nL, 50 nL to 500 nL, 60 nL to 70 nL, 60 nL to 80 nL, 60 nL to 90 nL, 60 nL to 100 nL, 60 nL to 200 nL, 60 nL to 300 nL, 60 nL to 400 nL, 60 nL to 500 nL, 70 nL to 80 nL, 70 nL to 90 nL, 70 nL to 100 nL, 70 nL to 200 nL, 70 nL to 300 nL, 70 nL to 400 nL, 70 nL to 500 nL, 80 nL to 90 nL, 80 nL to 100 nL, 80 nL to 200 nL, 80 nL to 300 nL, 80 nL to 400 nL, 80 nL to 500 nL, 90 nL to 100 nL, 90 nL to 200 nL, 90 nL to 300 nL, 90 nL to 400 nL, 90 nL to 500 nL, 100 nL to 200 nL, 100 nL to 300 nL, 100 nL to 400 nL, 100 nL to 500 nL, 200 nL to 300 nL, 200 nL to 400 nL, 200 nL to 500 nL, 300 nL to 400 nL, 300 nL to 500 nL, 400 nL to 500 nL, 500 nL to 1000 nL, 600 nL to 1000 nL, 700 nL to 1000 nL, 800 nL to 1000 nL, 900 nL to 1000 nL, 1000 nL to 5000 nL, 1500 nL to 5000 nL, 1750 nL to 5000 nL, 2000 nL to 5000 nL, 2250 nL to 5000 nL, 2500 nL to 5000 nL, 2750 nL to 5000 nL, 3000 nL to 5000 nL, 3250 nL to 5000 nL, 3500 nL to 5000 nL, 3750 nL to 5000 nL, 4000 nL to 5000 nL, 4250 nL to 5000 nL, or 4500 nL to 5000 nL, 4750 nL to 5000 nL. In certain example embodiments the first reaction circuit has a volume of approximately 40 nL to approximately 500 nL, and the second reaction circuit has a volume of approximately 20 nL to approximately 200 nL. Each reaction module may have a volume of approximately 40 nL to approximately 5 μL.

The reaction circuit may have a width of approximately 0.2 mm to 5 mm, 0.2 mm to 4 mm, 0.2 mm to 3 mm, 0.2 mm to 2 mm, 0.2 mm to 1 mm, 0.2 mm to 0.9 mm, 0.2 mm to 0.8 mm, 0.2 mm to 0.7 mm, 0.2 mm to 0.6 mm, 0.2 mm to 0.5 mm, 0.2 mm to 0.4 mm, 0.2 mm to 0.3 mm, 0.5 mm to 1 mm, 0.5 mm to 1.5 mm, 0.5 mm to 2.0 mm, 0.5 mm to 2.5 mm, 0.5 mm to 3 mm, 0.5 mm to 3.5 mm, 0.5 mm to 4 mm, 0.5 mm to 5 mm, 1 mm to 5 mm, 2 mm to 5 mm, 3 mm to 5 mm, or 4 mm to 5 mm.

Figure 4:
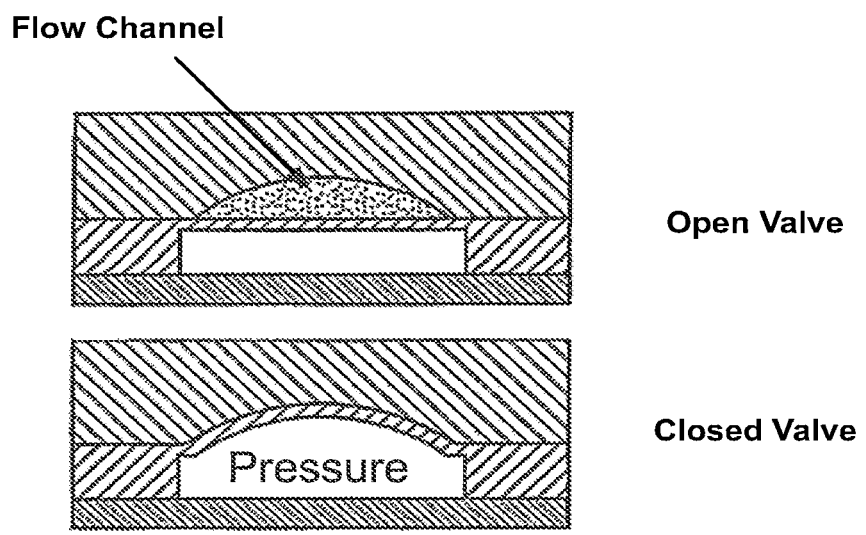
FIG. 4 is a diagram depicting an example microfluidic device valve in accordance with certain example embodiments.

The valves may be elastomeric valves that fully or partially occlude a flow channel when pressure is applied to the elastomeric material. For example, fluid channels may be located above or below a "control" layer of the microfluidic device. The control layer includes an elastomeric membrane that can be deflected to partially or completely block the flow channel. See FIG. 4. Suitable elastomeric materials include any material having a Young's modulus less than a metal. For example, the valves can have a Young's modulus of less than about 10 gPa, less than about 5 gPa, less than about 1 gPa, less than about 0.1 gPa, less than about 0.01 gPa, or less than about 0.0001 gPa. In certain example embodiments, the valves can have a Young's modulus of between 200 KPa and 1000 KPa. In certain other example embodiments, the valves can have a Young's modulus of 300 Kpa and 900 KPa. In yet another example embodiment, the valve has a Young's modulus of 360 KPa to 870 KPa. In certain example embodiments, the elastomer is made from PDMS, polytetrafluoroethylene (PTFE), urethanes, other silicones, or perfluoropolyethers. Valves can be closed using fluid pressure, gas pressure, or any other suitable mechanism applied through a channel in the control layer and running under the elastomeric membrane to deflect the membrane into the fluid channel. For example, the valves can be actuated by injecting gases (e.g. air, nitrogen, argon), liquids (e.g., water, silicone oils, fluorinated oils, and other oils), solutions containing salts and/or polymers (including, but not limited to, polyethylene glycol, glycerol, and carbohydrates), and the like into the control channel. In addition to elastomeric valves actuated by pressure-based actuation system, monolithic valves with an elastomeric component and electrostatic, magnetic, electrolytic, and electrokinetic actuation systems as discussed, for example, in U.S. Pat. No. 6,767,706 and U.S. Patent Application Publication Nos. 2002/0109114 and 2002/0127736 may be used in certain example embodiments. Valves may also be closed by pressing a pin on the top of the flow channel to collapse the channel, for example, a pin actuated by a step motor or piezoelectric actuator. In such embodiments, a separate control channel is not required.

Figure 5:
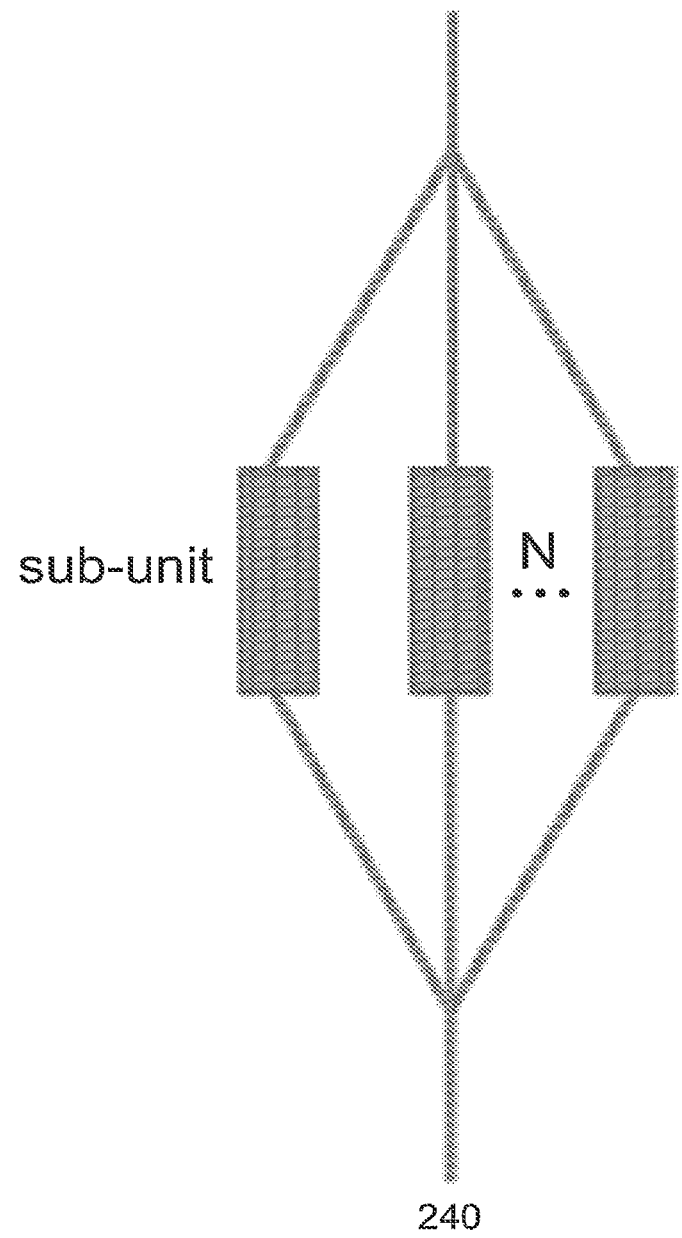
FIG. 5 is a diagram depicting an example filter unit comprising multiple sub-units, in accordance with certain example embodiments.

In certain example embodiments, filters that may be used in the present invention may have features similar to the valves described above, but instead of closing the fluid channel completely, the filter may only partially close the fluid channel, for example, to filter components in the fluid based on size. The filter unit (240) may comprise a single unit or multiple sub-units, for example, aligned in parallel fashion. Referring to FIG. 5, a sample design of a filter 240 comprising multiple filter sub-units is provided. In one example embodiment, the filter 240 comprises 1 to 10 sub-units. The width of each sub-unit may be between 0.05 mm to 0.5 mm. The length of each sub-unit may be between 0.05 mm and 1 mm. The reaction channel feeding the filter may branch as it approaches or enters the filter unit to break the flow into separate individual streams flowing into each individual sub-unit. Flow channels exiting the individual filter units may then re-converge into a single flow channel. In certain example embodiments, the filters may be used in a bi-directional fashion to provide filtering of a solution regardless of the direction in which the solution is passed through the filter unit. The size of flow channels entering and exiting filter subunits may have the dimensions defined above for flow and bridge channels.

An example filter unit is provided in FIG. 6. The example filter unit and/or each individual filter sub-unit comprises a base substrate (605) with a set of individually spaced teeth (610). The teeth represent a raised portion extending above the surface of the base substrate. The bottom substrate (605) may have a height of between 0.1 mm to 0.03 mm and a width of 0.05 mm to 0.5 mm. The teeth (610) may have a height of 0.001 mm to 0.15 mm, a width of 0.01 mm to 0.03 mm, and a length of 0.05 to 1 mm. The number of teeth in a filter sub-unit may range from 1 to 10 teeth. The number of teeth in each sub-unit may be the same or different. In certain example embodiments, the filter is made using the elastomeric materials described and is operated by application of pressure via a control valve the deflects the base substrate and teeth into a flow channel, thereby partially blocking the flow of solution through the filter or each filter sub-unit. The teeth may be sized to retain a capture substrate or other solid material to be used on the microfluidic device.

In certain other example embodiments, the filter may comprise a toothed sieved valve. See FIG. 7. Toothed sieve valves are disclosed in further detail in International Patent Application No. PCT/US14/58637.

Figure 8:
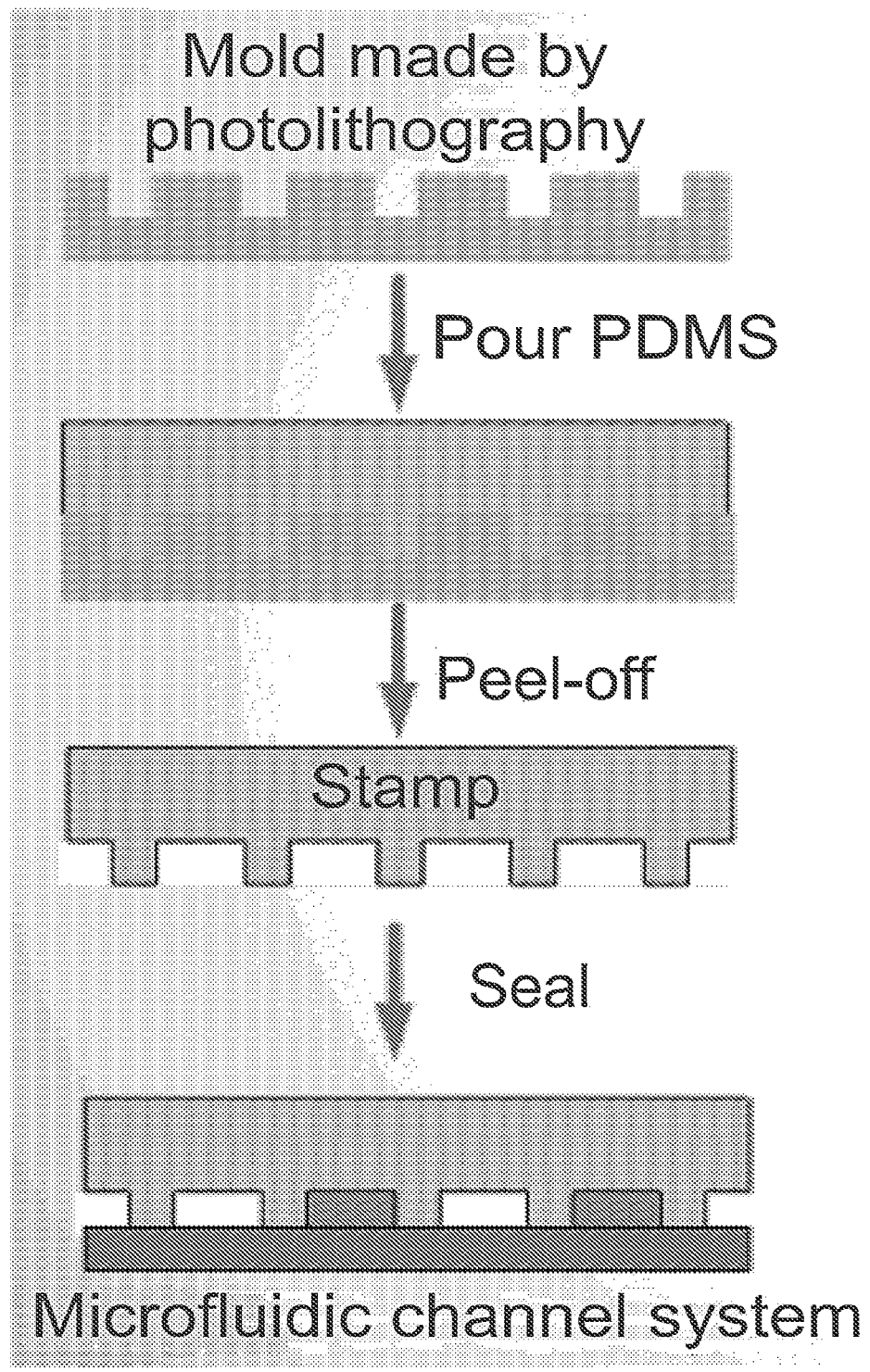
FIG. 8 is a diagram depicting an example microfluidic device manufacturing process, in accordance with certain example embodiments.
Figure 9:
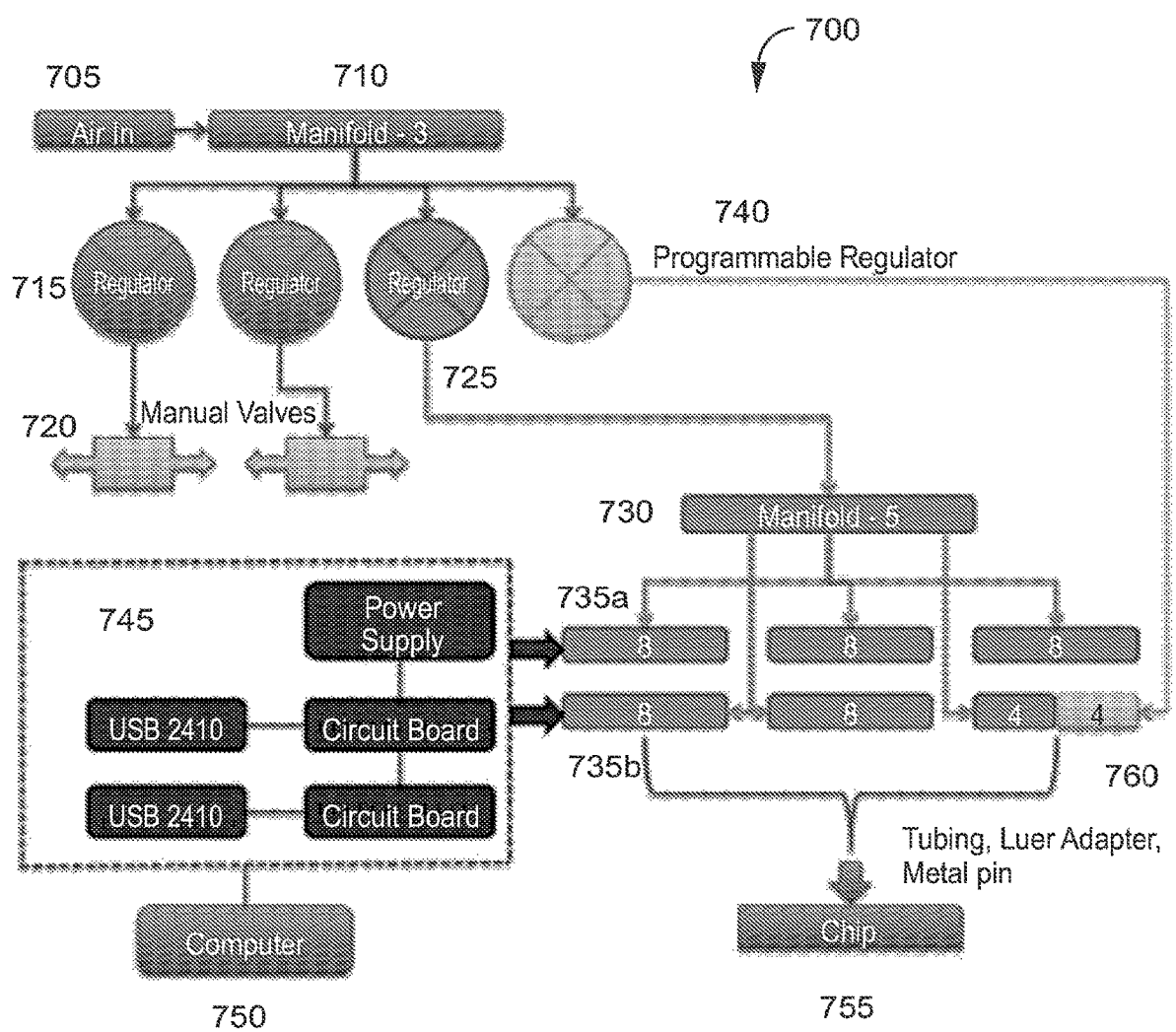
FIG. 9 is a diagram depicting an example microfluidic device controller system in accordance with certain example embodiments.
Figure 10:
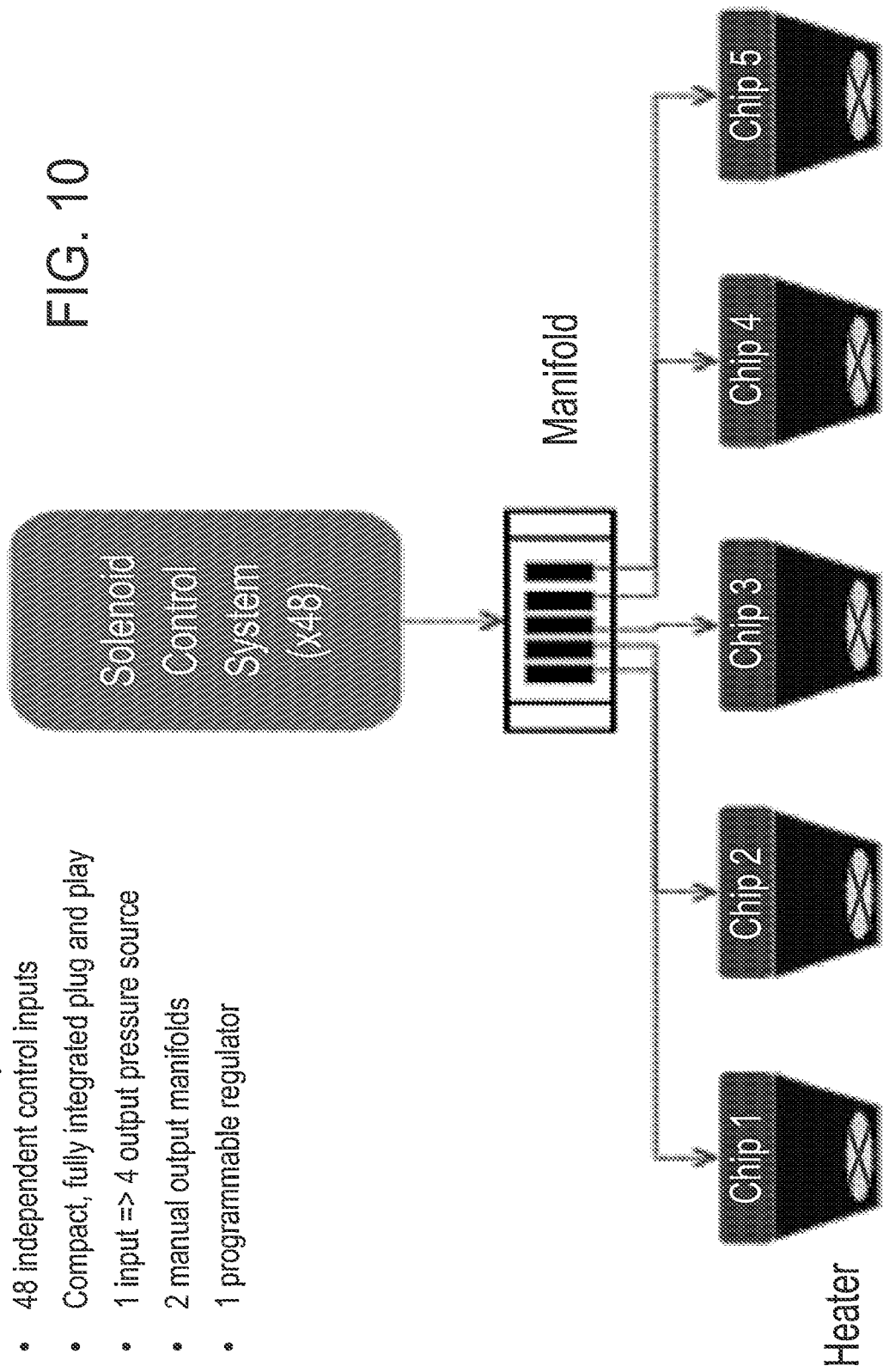
FIG. 10 is a diagram depicting an example microfluidic device controller system in accordance with certain example embodiments.

Microfluidic devices disclosed herein may be silicone-based chips and may be fabricated using a variety of techniques, including, but not limited to, hot embossing, molding of elastomers, injection molding, LIGA, soft lithography, silicon fabrication and related thin film processing techniques. Suitable materials for fabricating the microfluidic devices include, but are not limited to, cyclic olefin copolymer (COC), polycarbonate, poly(dimethylsiloxane) (PDMS), and poly(methylacrylate) (PMMA). In one embodiment, soft lithography in PDMS may be used to prepare the microfluidic devices. For example, a mold may be made using photolithography which defines the location of flow channels, valves, and filters within a substrate. The substrate material is poured into a mold and allowed to set to create a stamp. The stamp is then sealed to a solid support, such as but not limited to, glass. See, for example, FIG. 8.

Due to the hydrophobic nature of some polymers, such as PDMS, which absorbs some proteins and may inhibit certain biological processes, a passivating agent may be necessary (Schoffner et al. Nucleic Acids Research, 1996, 24:375-379). Suitable passivating agents are known in the art and include, but are not limited to, silanes, parylene, n-Dodecyl-b-D-maltoside (DDM), pluronic, Tween-20, other similar surfactants, polyethylene glycol (PEG), albumin, collagen, and other similar proteins and peptides.

The microfluidic devices may further comprise inlet and outlet ports, or openings, which in turn may be connected to valves, tubes, channels, chambers, and syringes and/or pumps for the introduction and extraction of fluids into and from the microfluidic device. The microfluidic devices may be connected to fluid flow actuators that allow directional movement of fluids within the microfluidic device. Example actuators include, but are not limited to, syringe pumps, mechanically actuated recirculating pumps, electroosmotic pumps, bulbs, bellows, diaphragms, or bubbles intended to force movement of fluids. In certain example embodiments, the microfluidic devices are connected to controllers with programmable valves that work together to move fluids through the microfluidic device. In certain example embodiments, the microfluidic devices are connected to the controllers discussed in further detail below. The microfluidic devices may be connected to flow actuators, controllers, and sample loading devices by tubing that terminates in metal pins for insertion into inlet ports on the microfluidic device.

Microfluidic Device Controller Systems

The embodiments herein include microfluidic device controller systems comprising a controller with one or more controllable valves, which may be programmable. The controller system may provide a portable system with an arrangement, such as an array, of valves that can be used to provide a series of different pressure inputs, either manually, automatically or in a pre-programmed manner, to a microfluidic device or set of microfluidic devices run in parallel. The ability to provide multiple programmable pressure inputs to a microfluidic device allows for the coordinated operation of multiple valves to move fluids through the microfluidic device. The controller systems can be used with a variety of microfluidic devices and include a graphical user interface (GUI) for easy control of pressure inputs and other parameters on the device.

In certain example embodiments, the controller systems disclosed herein comprise one or more microfluidic devices, a controller, and a display device configured to render a graphical user interface. The systems may further comprise a thermal control unit for controlling temperatures on the microfluidic device or devices, a sample loading device, and a machine vision device for monitoring the chip surface. In certain example embodiments, the thermal control unit may be a thermocycler that subjects the microfluidic device to a series of differing temperatures, for example to support nucleic binding and amplification on the microfluidic device.

The microfluidic device can be any microfluidic device. In certain example embodiments, the microfluidic device or devices comprises the microfluidic devices disclosed herein. In certain example embodiments, the controller may control up to 2, 4, 8, 12, 16, 20, 24, 28, 32, 36, 40, 44, 48 or more microfluidic devices.

In certain example embodiments, the controller comprises a first array of programmable valves, a second array of programmable valves, at least one output manifold, two or more air regulators to connect with an air source, one or more control boards communicatively coupled to the first and second array of programmable valves, a storage device, and a processor communicatively coupled to the storage device and the one or more control boards.

Figure 7:
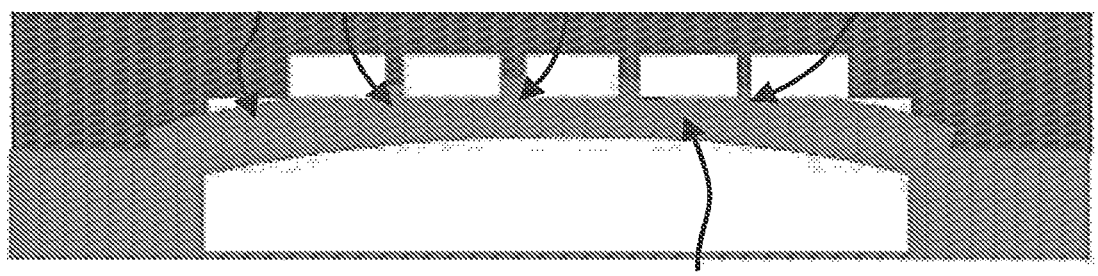
FIG. 7 is a diagram depicting an example microfluidic device filter in accordance with certain example embodiments.

Referring to FIG. 7, in one example system, the controller system 700 comprises an air source 705, and a first input manifold 710, one or more regulators 715 connected to one or more manual valves 720, a regulator 725 connected to a second input manifold 730, a first and second set of programmable valves 735a and 735b, a programmable regulator 740, a controller 745, a computer/display device 750, and one or more microfluidic devices 755. The programmable regulator 740 may be connected to a sub-set of programmable valves 760. The sub-set of programmable valves 760 connected to the programmable regulator 740 may be used to test various pressures while the one or more microfluidic devices are in use, allowing for pressure modifications to be made to the one or microfluidic devices while in operation.

The controller may comprise a power supply, one or more controllers, and one or more communication links between the circuit boards and the controller computer 750. In one example embodiment, a first circuit board controls the first set of programmable valves 735a, and a second circuit board controls the second set of programmable valves 735b. In certain example embodiments, the first set and second set of programmable valves can be grouped into sub-groups. In one example embodiment, the first set of programmable valves are grouped into three sets of eight, and the second set of programmable valves are grouped into two sub-groups of eight, a first sub-group of four, and a second sub-group of four. Other groupings may be used or the valves may be operated as a single unit. In certain example embodiments, the programmable valves are grouped into sub-groups according to the number of microfluidic devices controlled by the controller system, with the number of programmable valves equal to the number of different pressure inputs needed to operate components or groups of component parts on the device, such as filters and valves. In certain example embodiments, the controller system may comprise between 2 and 96 programmable valves. In certain example embodiments, the controller system comprises at least 48 programmable valves. In certain example embodiments, the programmable valves are solenoid valves. In addition, the controller may include necessary heat transfers, heat sinks, power supplies, and manual or electronic regulators.

The second circuit board in combination with the programmable regulator 740 may be used to apply a range of pressures to the microfluidic devices while the microfluidic devices are in use. For example, most microfluidic devices have a standard operating pressure, e.g., in the flow channels or in the control lines, however that pressure can change over the course of the use of the microfluidic device.

Figure 15:
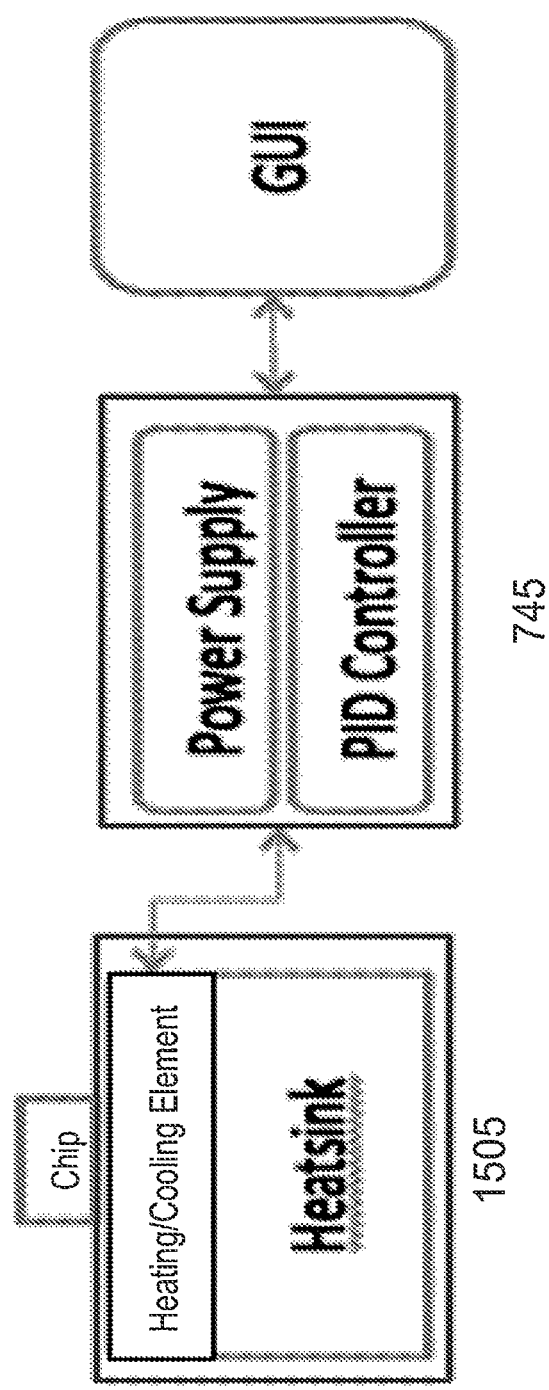
FIG. 15 is a diagram depicting the placement of an example thermal unit within the microfluidic device controller system, in accordance with certain example embodiments.

The microfluidic device controller systems may further comprise a thermal unit to heat and cool the microfluidic device during operation. The thermal unit may comprise a heating and cooling element connected via a communication link to the controller. The controller may control heating and cooling cycles for example via the first and/or second control circuit boards. In certain example embodiments, the power supply for the thermal unit may be provided by the controller. The thermal unit may comprise any heating or cooling element known in the art. In certain example embodiments, the thermal unit comprises a peltier module that functions as both a heater and cooler. A top surface of the thermal unit is configured to received one or more microfluidic devices. In certain example embodiments, the top surface may comprise one or more recesses that receive the one or more microfluidic devices. In certain other example embodiments, the recess may be adjustable to conform to different sizes of microfluidic devices. In certain example embodiments, the thermal unit further comprises a heat sink attached to the heating/cooling element. FIG. 15 provides a diagram showing the relative position of an example thermal unit relative to the other elements of the microfluidic device controller system.

The microfluidic device controller systems enable the ability to do on the fly pressure adjustments to account for these fluctuations while the microfluidic device is in use. In addition to on the fly pressure regulation, the controller systems also enable closed-loop tuning of microfluidic devices. For example, certain component parts of a microfluidic device, such as valves and filters, have a manufacturing tolerance for certain pressures under which they will function properly. However, this tolerance may not be known. A microfluidic device can be connected to the controller system, the programmable regulator 740 and second sub-group of programmable valves may be programmed to expose each component on the microfluidic device to a range of pressure. A machine vision device, such as a machine vision camera, and/or flow sensor with controlled feedback, may be used to monitor the surface of the microfluidic device to determine the optimal pressure range at which the component part operates correctly. For example, the machine vision camera and/or flow sensor with controlled feedback may be used to determine the optimal pressure at which a valve or set of valves completely seals a fluid channel.

The controller computer may comprise a storage device and a processor. The controller computer 750 receives a microfluidic device protocol file. For example, the components of the device may be defined in a tab delimited or spreadsheet file format. The device protocol will define, among other things, a valve sequence at which each individual valve should be opened and closed to move fluids on the device. The controller computer 750 executes software that translates the raw information in the device protocol file and interfaces with the controller to operate the necessary components, such as valves or other components on the microfluidic devices, to move the fluids on the microfluidic device as desired. For example, a feedback system established between the controller computer 750 and the microfluidic devices and sensors may allow the programmable regulator and the programmable valves to adjust pressures to the microfluidic device within certain tolerances, pressures and/or parameters or the like. The controller computer 750 may also render a GUI comprising a "virtual" microfluidic device architecture.

Figure 13:
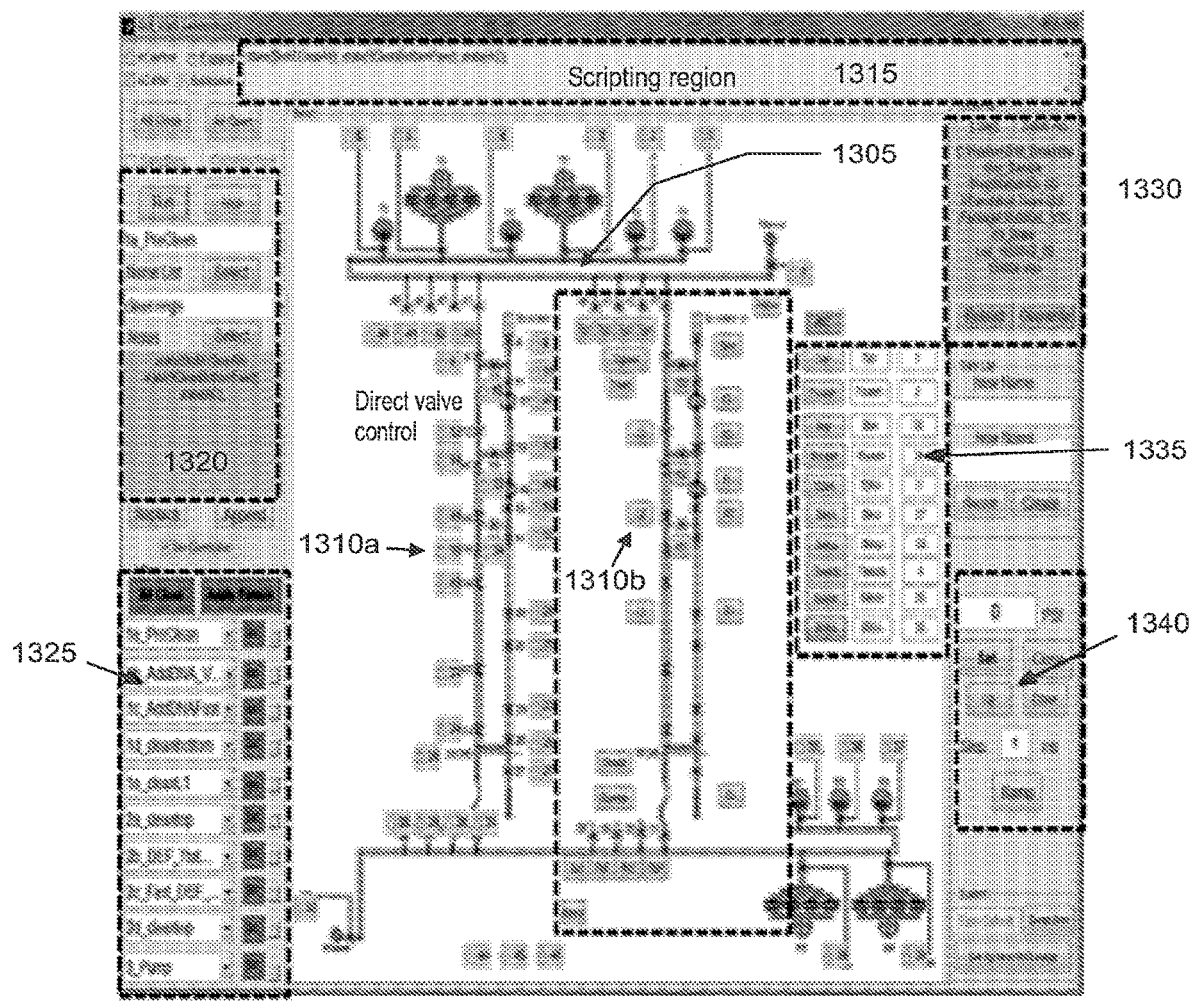
FIG. 13 is an image depicting an example graphical user interface, in accordance with certain example embodiments.
Figure 14:
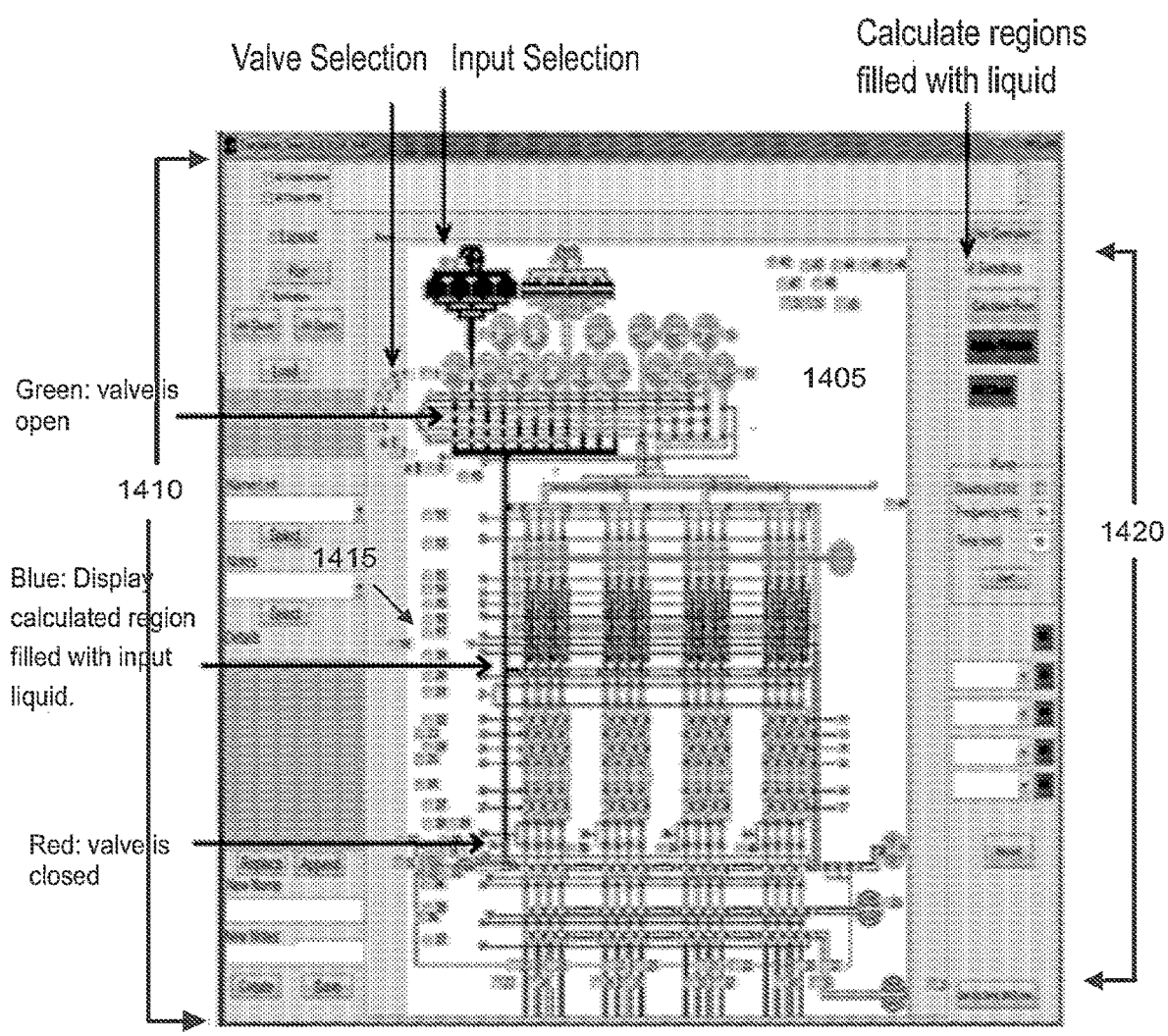
FIG. 14 is an image depicting another example graphical user, in accordance with certain example embodiments.

The GUI may allow a user or operator to select individual component parts on the virtual microfluidic device architecture parameters to control and modify operation of the individual components easily. Example GUIs are shown in FIGS. 13 and 14. The GUI may also comprise a simulation mode allowing for visual protocol development prior to running a live protocol on a microfluidic device. The GUI may be overlaid on a visual representation of the actual device, either in schematic or an actual enlarged video image of the device in operation (real-time).

In one example embodiment, the controller computer may execute computer-programmable instructions that render a GUI in an operation interface configuration or a simulation interface configuration. An example operation interface configuration is shown in FIG. 13. The operation interface (1300) may comprise a microfluidic device layout portion 1305 representing a virtual layout of the actual microfluidic device connected to the controller, including the relative positioning of reaction flow channels, pumps, values, input/output lines, reaction circuits, valves and filters. The device architecture, that is the relative layout of device elements, may be defined and stored in device layout file that is loaded onto the controller computer. Alternatively, the microfluidic device architecture portion 1305 may further comprise a device build portion (not shown) comprising a graphical representation of as set of predefined device elements—such as filter, valves, flow channels, pumps, or pre-defined reaction circuits and modules etc.—wherein the device elements may be dragged and dropped onto the microfluidic device architecture portion 1305 and arranged to define a given microfluidic device architecture.

The device architecture portion may further comprise selectable elements 1310a, such as radial buttons, drop-down menus etc., located proximate to various elements indicated on the device architecture portion and that allow a user to control the corresponding element. The selectable element may be displayed proximately to each individual element on the device that can be controlled by the system. Alternatively various elements, such as a group of valves and/or filters, may be grouped and controlled by a single selectable element 1310b such that selection and de-selection activates and deactivates the corresponding elements as a group.

The operation interface 1300 may further comprise other control portions. For example, the operation interface may comprise a scripting portion 1315 that allows users to directly enter command scripts to control operation of the microfluidic device, a command portion 1320 comprising a set of selectable elements and/or data entry field that allow a user to select a pre-defined protocol file such as that described in paragraph 58, a shortcut portion 1325 that allows a user to select a pre-defined protocol from a list of commonly used protocols, a file operation portion 1330 that allows a user to select and upload a new protocol file, a dynamic input portion 1335 that allows a user to change an input port without modifying a script, and a digital regulation portion 1340 that sets and/or change pressure in a predefined way. The operation interface 1300 may also be configured so that selection of a protocol in any of the control portion causes the device architecture portion to automatically update to show the selected elements, e.g. which valves are opened or closed. Likewise, the operation interface 1300 may be configured so that a selected protocol may be modified by selecting and de-selecting various elements on the device architecture portion 1305 resulting in automatic modifications to the commands in the corresponding device protocol file.

In another example embodiment, the controller computer may execute computer-programmable instructions that render a GUI in an simulation interface configuration. An example simulation interface configuration is shown in FIG. 14. The simulation interface comprise a microfluidic device layout portion 1405 representing a virtual layout of the actual microfluidic device connected to the controller, including the relative positioning of pumps, input/output lines, reaction circuits, valves and filters. The microfluidic device layout portion 1405 may further comprise selectable elements 1415, such as radial buttons, drop-down menus etc., located proximate to various elements indicated on the device architecture portion and that allow a user to control the corresponding element. For example, selecting the selectable element 1415 may open the corresponding valve and de-selecting the selectable element may close the corresponding valve, or vice versa. The selectable element may be displayed proximately to each individual element on the device that can be controlled by the system.

The simulation interface further comprises a control portion 1410 comprising selectable control elements for loading and running test protocols, and a test parameter portion 1420 comprising selectable elements and fields for setting various physical parameters such as flow and pressure changes during a given protocol, or to allow a subset of elements on the device architecture portion to be selected and isolated to test certain assay parameters. For example, a user may test a step in a given protocol by selecting a set of valves to be opened or closed, select an input source, set pressure and flow parameters, and then select a "calculate flow" element in the test parameter portion 1420. The interface then updates to show the channels on the microfluidic device that will be filled based on the selected parameters and valve combinations. In this way, a user may fine tune protocols to ensure optimal and efficient reagent flow prior to loading actual reagents on the physical microfluidic device. The simulation interface may also be configured to run a test simulation of a complete protocol. After selection of a test protocol file to run using the control portion 1410, the device architecture portion 1405 will update over the course of the protocol run to indicate which valves are open, actively pumping, or closed, and which channels are filled and emptied during the various steps of the selected protocol. In certain example embodiments, a user may switch back and forth between the operation and simulation interfaces, for example, by selecting a button or other element displayed on the respective interface.

Applications

The microfluidic devices and controller systems disclosed herein can be used in methods for processing samples that require volume metering, mixing, filtering, solid phase reversible immobilization substrate binding, or a combination thereof. The devices and systems are particularly well-suited to precious samples, such as certain clinical samples, that are only available in small volumes. In certain example embodiments, the microfluidic devices are used for processing biological samples. In certain other example embodiments, the microfluidic devices are used for processing nucleic acid samples such as processing DNA/RNA for library preparation and hybrid selection for exome and whole genome sequencing. For example, the microfluidic devices disclosed herein may be used to prepare clinical samples from diseased tissue for downstream sequencing using various NGS technologies. Likewise, the microfluidic devices disclosed herein may be used to process pathogen isolates for downstream sequencing using various NGS technologies.

In certain example embodiments, a method for processing a biological sample comprises loading a first reagent into a first reaction circuit of a reaction module. A second reagent is then loaded into a second reaction circuit of the reaction module. In the case where each reaction module comprises only a single reaction circuit, such as in a node arrangement, the second reagent may be loaded into a second reaction module. The first and second reagents are merged by mixing the first and second reagents between the first and second reaction circuits to generate an analyte. After the analyte is generated, the analyte is retained in one of the reaction circuits. A capture substrate is then loaded into the other reaction circuit. The analyte and capture substrate are then mixed between the first and second reaction circuits to allow the capture substrate to bind the analyte. The solution containing the capture substrate is then passed through a size exclusion filter, or other appropriate filter, to retain the capture substrate with bound analyte in at least one portion of the reaction circuit. The retained capture substrate can then be washed repeatedly with a wash buffer. The filter is then opened and the capture substrate with bound analyte eluted out of the reaction module and out of the microfluidic device. Other methods for filtering, washing, and eluting can be used according to the protocols and structures of the microfluidic device.

Figure 11:
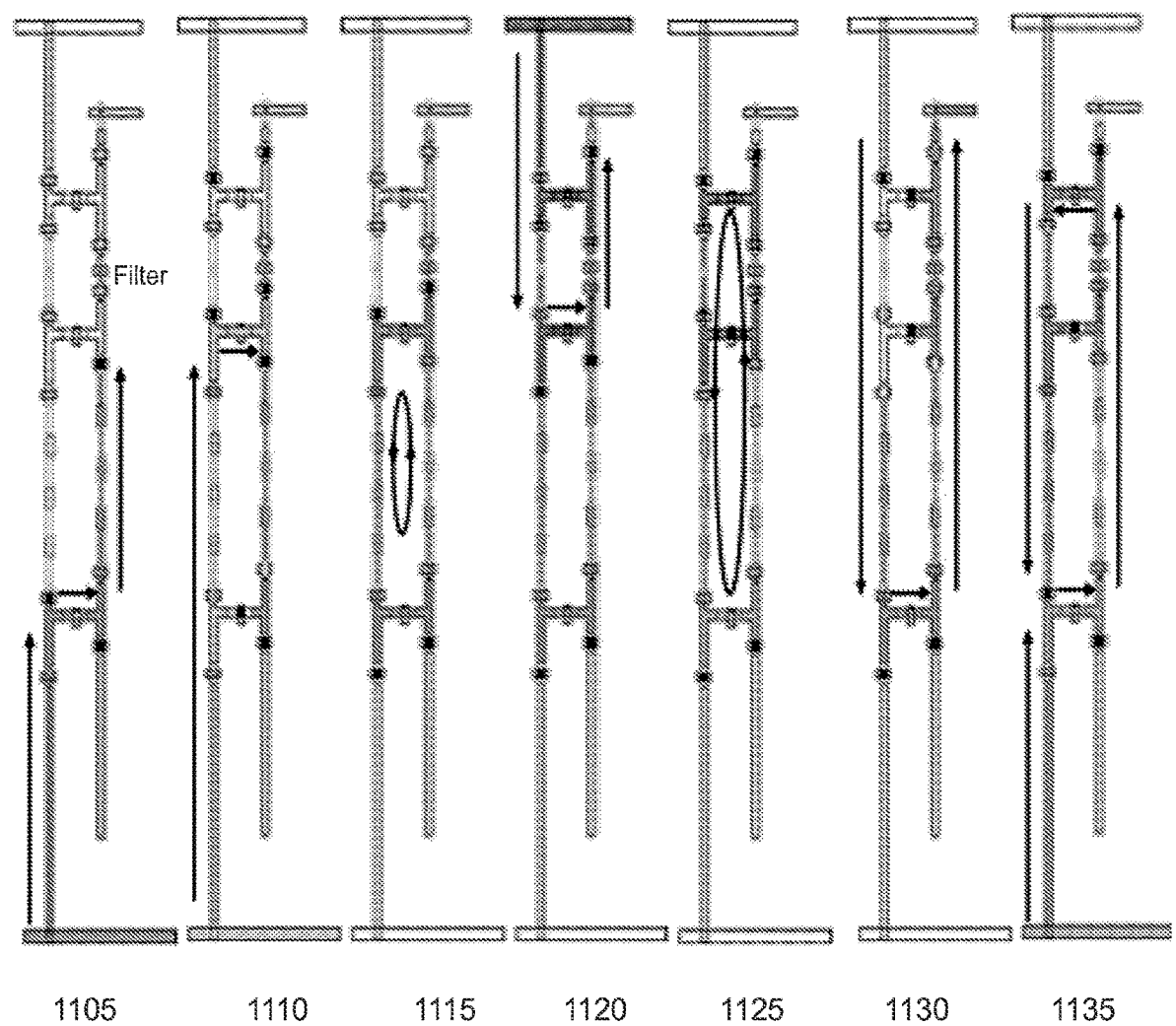
FIG. 11 is a diagram depicting an example process for processing samples using microfluidic devices disclosed herein and in accordance with certain example embodiments.

In certain example embodiments, a method for processing biological samples comprises use of the microfluidic device described herein. Referring to FIG. 11, a method for processing a biological sample according to an example embodiment comprises, opening and closing valves on the reaction module according to the pattern at 905 and in order to fill the second reaction flow channel of a first reaction circuit with a first reagent; opening and closing valves according to the pattern indicated at 910 to fill the first reaction flow channel of a first reaction circuit with a second reagent; opening and closing valves according to the pattern at 915 to mix the first and second reagent between the first and second reaction flow channels of the first reaction circuit in order to generate an analyte, opening and closing valves according to the pattern at 920 to fill both the first and second reaction flow channels of a second reaction circuit with a capture substrate; opening and closing valves according to the pattern at 925 to mix the capture substrate and the analyte between the first and second reaction circuits to allow for binding of the analyte to the capture substrate, opening and closing valves, and activating a filter on the second reaction circuit, according to the pattern at 930 to wash the capture substrate with bound analyte while retaining the capture substrate on the reaction module; multiple washes may be performed according to the needs of the exact protocol being performed; opening and closing valves according to the pattern at 935 to elute the capture substrate with bound analyte from each reaction module and out of the microfluidic device. In certain example embodiments, samples from each reaction module may be collected separately. In certain other example embodiments, samples from each reaction module may be pooled into a single sample. The above steps are by way of example only. Additional steps may be included prior to eluting the sample out of the reaction module. For example, the capture substrate with bound analyte may be pumped back to the first reaction circuit, a third set of reagents added to the second reaction circuit, and the capture substrate with analyte and third reagent mixed between the first and second reaction circuits. As can be observed in FIG. 11, reaction circuits of various volumes may be "recruited" by changing which valves are opened and closed. Because the reaction flow channels can be opened and washed and reused, the presently described device may be used for varied reactions. Thus, volumes of various ones of the reaction circuits may be substantially the same or different.

In one example embodiment, the first reagents are cells. For example, the cells may be normal or diseased tissue samples from a subject, or pathogen cells such as, but not limited to, clinically isolated bacterial or fungal cells. The second reagent is a lysis reagent to lyse the cells. The cells and lysis reagent are then mixed together in a first reaction circuit to allow for release of nucleic acid material. The cell lysate is then retained in the first reaction circuit and the second reaction circuit is filled with tagmentation reagents to simultaneously fragment and label the resulting fragments with sequencing primers. The first and second reaction circuits are mixed to allow for tagmentation of the nucleic acid material. The tagmented nucleic acid material is retained in the first reaction circuit and a capture substrate is added to the second reaction circuit. The first and second reaction circuits are mixed to allow binding of the tagmented nucleic acid material to the capture substrate. A filter, such as a sieve valve, is used to retain the capture substrate in the reaction module and the bound tagmented nucleic acid material may be washed one or more times. The washed capture substrate is then retained in the first reaction circuit and PCR and barcoding reagents are added to the second reaction circuit. The first and second reaction circuits are mixed to allow for barcoding and PCR amplification of the tagmented nucleic acid material. The reaction buffer may be formulated so that the tagmented nucleic acid material bound to the capture substrate is released. The resulting barcoded amplicons are then eluted from each reaction module for sequencing. The amplicons may be pooled and sequenced in bulk using NGS technology and the sequences deconvoluted to reaction module/sample of origin using the encoded barcode information in the amplicon sequencing data.

Alternatively, the above method could be modified so that the capture substrate is added after lysis of the cells. The capture substrate and bound nucleic acid material are then retained in the first reaction circuit. Tagmentation reagents are then added to the second reaction circuit. The first and second reaction circuits are mixed to allow for tagmentation of the nucleic acid material. The tagmentation reaction buffer may be formulated so that the nucleic acid material is released from the capture substrate. The released nucleic acid material may then be separated from the capture substrate, for example using a size exclusion filter, and the capture substrate eluted off the reaction module. After a sufficient time, the tagmented nucleic acid material may be retained in the first reaction circuit and a stop solution added to the second reaction circuit. The first and second reaction circuits are then mixed to stop the tagmentation reaction. The tagmented nucleic acid material may then be retained on the first reaction circuit and the capture substrate step repeated to bind tagmented nucleic acid material. The capture substrate may then be washed as described above. The capture substrate with bound tagmented nucleic acid material is then eluted from the microfluidic device. Enrichment PCR and barcoding steps may then be performed off the microfluidic device and prior to sequencing.

The capture substrates referenced above may be any capture substrate that specifically binds the analyte of interest, provided the capture substrate can reversibly bind the analyte of interest. For capturing nucleic acids, the capture substrate can be any substrate that binds nucleic acids in its activated state, such as solid phase reversible immobilization (SPRI) capture beads or any other suitable substrates that can capture a nucleic acid. A non-limiting example of a capture substrate that can be used to capture nucleic acids is DYNABEADS® capture beads available from Life Technologies of Carlsbad, California. In certain example embodiments, the capture substrate can be configured to capture a protein, such as hemoglobin, antibodies, carbohydrates, small molecules, or any cellular component of interest. In certain example embodiments, the capture substrate may require an activation agent to bind the analyte of interest. While activated, the capture substrate selectively binds the analyte of interest, such as a nucleic acid. A non-limiting example of an activation agent is 20% polyethylene glycol (PEG) and 2.5 M NaCl. The size of the capture substrate may be used to selectively filter the capture substrate on the chip. For example, the use of a size exclusion filter, such as a sieve valve, may allow for retention of the capture substrate within defined portions of a reaction circuit.

Examples of use of a microfluidic device according to aspects of the present invention are set forth below.

EXAMPLES

Example 1: Protocols for Hybrid Selection Using 16×400 nL Chip

1. Prime channels with surfactant
   1.1. 0.5% Pluronic F-127, 0.5% Kolliphor P188, 5% Tween 20, in Milli-Q water; syringe filter if possible.
   1.2. Filling in as much channel as possible.
   1.3. Incubate 1 hr;
   1.4. Purge channel w/air;
2. Rinse w/Wash Buffer
   2.1. 1% Tween 20 in Tris HCl buffer
   2.2. Wash; purge w/air;
   2.3. Repeat 3×;
3. Load Hybridization mixture to right ring (FIG. 11, 1105)
   3.1. Hybridization mixture (168.75 ul Enrichment hybridization buffer 1 from Kit (EHB)+31.25 ul concentrated (2×) oligoes, add to make 0.1% Tween, 50 ul)
   3.2. Script 3a_LoadHybMix; Dead-end fills bottom common feed
   3.3. Script 3b_LoadHybMix; Dead-end fills right side of the first ring
   3.4. Script 3c_ClearHybMix; Flushes bottom common feed with air
4. Load DNA target to left ring (FIG. 11, 1110)
   4.1. DNA target solution (19.53 ng/ml library; 0.1% Tween; 50 ul in a sharp pipette tip);
   4.2. Script 4a_LoadDNA; Dead-end fills bottom common feed with DNA target
   4.3. Script 4b_LoadDNA; Dead-end fills left side of the first ring 4.4. Script 4c_ClearDNA; Flushes bottom common feed with air
5. Hybridization (FIG. 11, 1115)
   5.1. Script 5a_MixHybRxn; Mixes ring contents CCW for 5 minutes at 20 Hz and 5 minutes CW at 20 hz (room temp)
   5.2. Flat-top thermocycler Hyb-1 (target 94C 10 min, step down, 2C/min; till 58C, hold for at least 90 min (~120 min);
   5.3. At 58 C, Script 5b_MixDuringHyb; Mixes ring contents CCW for 2 minutes at 20 Hz, pauses 10 minutes and repeats 10×;
6. Load capture beads; (FIG. 11, 1120)
   6.1. Streptavidin Magnetic Beads (SMB, 1 μm streptavidin beads) from Illumina kit, mix with 5 μm Frit beads (1:50 ratio).
   6.2. Script 6a_LoadCaptBeads; Dead-end fills top common feed;
   6.3. Script 6b_LoadCaptBeads; Dead-end fills left ring of the second ring;
7. Mix capture beads (FIG. 11, 1125)
   7.1. Room temperature;
   7.2. Script 7a_Ringmerge; merge the first and the second ring;
   7.3. Script 7b_CaptMix; Mixes ring contents CCW for 5 minutes at 20 Hz and 5 minutes CW at 20 hz; Make sure the filter valve is open;
   7.4. Script 7c_CaptMix; Mixes ring contents CCW for 1 minute, CW for 1 minute at 20 Hz every, pauses 10 minutes and repeats 3×;
8. Filter capture beads
   8.1. Script 8a_FilterBead; Slowly ramp up pressure on the filter valve, while mixing, till a plug of beads are forming in front of the filter
   8.2. Script 8b_FilterBead; Increase the pressure on the filter valve to 20 psi. Flushes the entire ring with air from top common feed through filter to sewer port
9. Wash capture beads (Stringency wash) (FIG. 11, 1130)
   9.1. Enrichment Wash Buffer (EWS) from Kit. (no tween added); use Falcon tube reservoir;
   9.2. Script 9a_LoadCaptWashBuf; Dead-end fills top common feed with EWS
   9.3. Script 9b_LoadCaptWashBuf; Dead-end fills the second ring;
   9.4. At 50 C; Script_9c resuspend; Open filter valve; mixes the second ring contents CCW for 5 minutes at 20 Hz and 5 minutes CW at 20 Hz; Beads should resuspend in the solution;
   9.5. Script 9d_FlushWashBuf; Flushes top common feed with air
   9.6. Script 9e_FlushwashBuf; Flush the second ring with air through filter valve to sewer;
   9.7. Repeat step 9.2-9.6 2×.
10. Elute DNA out from capture beads (FIG. 11, 1135)
    10.1. 285 ul Enrichment Elution Buffer 1 (EE1) from kit+15 ul 2N NaOH (HP3) from Kit; add 0.1% Tween;
    10.2. Script 10a_CaptElute; Dead-end fills bottom common with elute buffer
    10.3. Script 10b_CaptElute; Flows elution over beads and into left side of the first ring (in a U shape pathway) for 1 second, pause 10 sec, repeat till all reservoirs are filled up.
11. Wash out beads
    11.1. Wash Buffer;
    11.2. Script 11a_WashOutBeads; Dead-end fills top common feed with wash buffer;
    11.3. Script 11b_WashOutBeads; Flushes beads to sewer with filter valve open;
    11.4. Script 11c_ClearWash; Flushes top common feed with air;
    11.5. Script 11d_ClearWash; Flushes the second ring to sewer
12. Add Neutralization buffer
    12.1. Elute Target Buffer 2 (ET2, neutralization buffer) from Kit, add to 0.1% Tween;
    12.2. Script 12a_NeutBuf; Meters in neutralization buffer to the right side of the first ring;
    12.3. Script 12b_FlushNeutBuf; Mixes the first ring contents CCW for 5 minutes at 20 Hz and 5 minutes CW at 20 Hz to neutralize the eluted DNA.

As illustrated by the sequences set forth above, the microfluidic device according to aspects of the present application can be flushed via a top common feed through filter to a sewer port. A sewer port is formed by providing fluid communication between a control channel and a reaction flow channel such that application of fluid, such as air, water or any acceptable fluid, to the reaction flow channel forces the contents of the reaction flow channel into the control channel, which itself can be connected to an output or disposal channel or port. Any of the components in the flow channel layer, such as the reaction flow channel, bridge flow channels, valves, filters or the like can be flushed via this manner. Which components are actually flushed can be controlled by controlling which valves are open or closed during the flush, forcing the flushing fluid through a selected path to the sewer port and out of the device. According to aspects of the present application, a single sewer port or multiple sewer ports may be provided per device.

Example 2: Protocols for Tagmentation Using 16×400 nL Chip

1. Prime channels with surfactant
   1.1. 0.5% Pluronic F-127, 0.5% Kolliphor P188, 5% Tween 20, in Milli-Q water; syringe filter if possible.
   1.2. Filling in as much channel as possible.
   1.3. Incubate 1 hr;
   1.4. Purge channel w/air;
2. Rinse w/Wash Buffer
   2.1. 1% Tween 20 in Tris HCl buffer
   2.2. Wash; purge w/air;
   2.3. Repeat 3×;
3. Load tagmentation master mix to larger reactor ring
   3.1. Tagmentation mix (2 uL genomic DNA at 5 ng/uL, 5 uL tagmentation buffer, 3 uL tagmentation enzyme (TDE1), 0.25 uL 10% Tween 20, 10.25 uL in a gel-loading pipette tip).
   3.2. Dead-end fill right side of the larger reactor ring.
   3.4. Dead-end fill left side of the larger ring.
   3.5 Flush bottom feeds with air
4. Tagmentation
   4.1. Flat-top thermocycler Tagment (hold 58 C 10 min)
5. Stop tagmentation
   5.1 Dead-end fill bottom 25 nL of the larger ring with stop buffer (10% SDS), pushing 25 nl of tagmentation reaction into smaller reactor ring (e.g FIG. 11, 1120).
   5.2 Mix ring contents CCW for 5 minutes at 20 Hz and 5 minutes CW at 20 hz.
6. Remove samples from chip
   6.1 Insert gel-loading tips into bottom outlets.
   6.2 Run wash buffer (2.1 above) through left side of the ring and into the tip for 5 seconds.

6.3 Run wash buffer through right side of the ring and into the tip for 5 seconds.

6.4 Remove tips and eject liquid into tubes.

As can be appreciated from the above examples, because the microfluidic device may be flushed and made ready for subsequent reactions, microfluidic devices disclosed herein are reusable. Moreover, the microfluidic device is "programmable" for different types of reactions by providing proper protocols for opening and closing of valves by control of the control channels in predefined sequences or patterns to provide for proper fluid movement through the flow channels and to recruit a reaction circuit of proper filtering and volume to conduct the desired process/reaction. Further, the microfluidic device may be made and sized for particular automated equipment such that it can be mass produced or "standardized." As such, the features of the present invention are not limited to the size and configurations disclosed herein, and such plurality of reaction modules described herein may be provided in any combination of volumes, reaction flow channels, bridge flow and valves/filters in combination with a control channel as may be appropriate for a given reaction and control device.

All publications, patents, and patent applications mentioned herein are incorporated by reference to the same extent as if each individual publication, patent or patent application was specifically and individually indicated to be incorporated by reference in its entirety. In the event of there being a difference between definitions set forth in this application and those in documents incorporated herein by reference, the definitions set forth herein control.

Various modifications and variations of the described methods, pharmaceutical compositions, and kits of the disclosure will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the present disclosure and including such departures from the present disclosure come within known customary practice within the art to which the invention.

What is claimed is:

1. A microfluidic chip system, comprising:
    a microfluidic device controller, comprising:
        a first input manifold connected to an outside air source;
        two or more air regulators connected to the first input manifold;
        a second input manifold connected to one of the two or more air regulators;
        a subset of controllable valves connected to the second input manifold via multiple input connections, wherein the subset of controllable valves includes at least a first set of controllable valves, a second set of controllable valves, and one or more output ports;
        one or more control boards communicatively coupled to the at least first set of controllable valves and the second set of controllable valves in the subset of controllable valves; and
        a processor communicatively coupled to a digital storage device and the one or more control boards, wherein the processor executes application code instructions that are stored in the digital storage device to cause the one or more control boards to sequentially open and close the controllable valves to apply multiple pressure inputs to components of the microfluidic device, according to defined protocols; and
    one or more microfluidic devices connected to the subset of controllable valves via the one or more output ports.

2. The microfluidic chip system of claim 1, further comprising one or more of:
    a graphical user interface (GUI), the graphical user interface providing a virtual representation of the microfluidic device including a position of component parts on the microfluidic device, wherein parameters for each component can be changed by selecting the component on the virtual representation of the microfluidic device.

3. The microfluidic chip system of claim 1, wherein the second set of controllable valves is connected to a second control board, the second control board controlling operation of each controllable valve in the second controllable valve set, and wherein the second set of controllable valves and the second control board are used to make pressure adjustments to the one or more microfluidic devices while they are in use.

4. The system of claim 1, further comprising a thermal unit operatively connected to the microfluidic controller.

5. The system of claim 1, wherein the first set of controllable valves is connected to a first control board, wherein the first set of controllable valves can be controlled to execute a microfluidic device protocol, the microfluidic device protocol defining a pressure to be applied by each controllable valve to a component or set of components on the one or more microfluidic devices.

6. The system of claim 1, wherein the second set of controllable valves is connected to a second control board, the second control board controlling operation of each controllable valve in the second controllable valve set.

7. The system of claim 6, wherein the second set of controllable valves and the second control board are used to make pressure adjustments to the one or more microfluidic devices while they are in use.

8. The system of claim 6, wherein the second set of controllable valves is controlled by the second control board to determine a control pressure for the one or more microfluidic devices or a component of the device.

9. The system of claim 1, wherein the first set of controllable valves comprises 40 individually controllable valves.

10. The system of claim 9, wherein the 40 individually controllable valves are grouped in five sets of eight, each set of eight controlling pressure inputs to a separate microfluidic device.

11. The system of claim 5, wherein at least one of the two or more air regulators is a controllable regulator, wherein the second set of controllable valves comprises a group of eight controllable valves, four of which are connected to the controllable regulator.

12. The system of claim 1, wherein the controllable valves are solenoid valves.

13. The system of claim 1, wherein the subset of controllable valves comprises at least five outputs for connecting to one or more microfluidic devices.

14. The system of claim 1, wherein the at least one of the two or more regulators is a controllable regulator connected to at least one controllable valve within the subset of controllable valves.

15. The system of claim 1, wherein the one or more microfluidic devices comprise a plurality of reaction modules, each reaction module comprising one or more reaction circuits, each reaction circuit comprising at least one reaction flow channel connected to at least one bridge flow channel.

16. The system of claim 15, wherein each reaction module in the plurality of reaction modules comprises one or more reaction circuits, each reaction module comprising a first reaction flow channel connected at a first end to a first input and connected at a second end to a second input, and a second reaction flow channel connected at a first end to a first output and connected at a second endo to a second output of sealed end.

17. The system of claim 16, wherein the first and second reaction flow channels are connected by three or more bridge flow channels.

18. The system of claim 17, wherein the first reaction flow channel, the second reaction flow channel, and each bridge flow channel comprises one or more valves that can be sequentially opened to pump fluids between the reaction circuits and on and off the reaction modules.

19. The system of claim 1, wherein the one or more microfluidic devices each comprise 1 to 384 reaction modules.

* * * * *